United States Patent [19]

Nakai et al.

[11] Patent Number: 4,777,178

[45] Date of Patent: Oct. 11, 1988

[54] THIAZOLIDINE DERIVATIVES

[75] Inventors: Hideo Nakai; Hiroshi Wada, both of Omiya; Taku Nagao, Tokyo; Hideo Yabana, Omiya, all of Japan

[73] Assignee: Tanabe Seiyaku Co., Ltd., Osaka, Japan

[21] Appl. No.: 870,915

[22] Filed: Jun. 5, 1986

[30] Foreign Application Priority Data

Jun. 15, 1985 [GB] United Kingdom ............... 8515212

[51] Int. Cl.⁴ .................. A61K 31/425; C07D 417/12
[52] U.S. Cl. .................................... 514/326; 514/342; 546/209; 546/280
[58] Field of Search ............... 546/209, 280; 514/326, 514/342

[56] References Cited

FOREIGN PATENT DOCUMENTS 212174 12/1982 Japan .................................. 548/146
41872 3/1983 Japan .................................. 546/280

Primary Examiner—Robert T. Bond
Attorney, Agent, or Firm—Birch, Stewart, Kolasch & Birch

[57] ABSTRACT

A novel thiazolidine derivative of the formula:

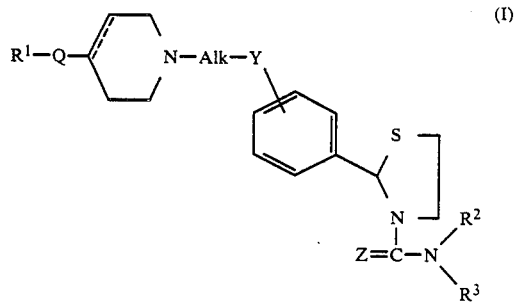

wherein $R^1$ is a substituted or unsubstituted phenyl group, $R^2$ is hydrogen or a lower alkyl group, $R^3$ is hydrogen, a lower alkyl group or a lower alkanoyl group, Q is a single bond or a lower alkylene group, Alk is a lower alkylene group, Y and Z are the same or different and are oxygen atom or sulfur atom and the group of the formula:

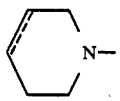

is either

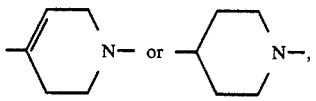

or a pharmaceutically acceptable salt thereof, which is useful as a cardiotonic agent is disclosed together with processes for the preparation of the compound and a pharmaceutical composition containing said compound.

21 Claims, No Drawings

THIAZOLIDINE DERIVATIVES

The present invention relates to a novel thiazolidine derivative, a salt thereof, processes for preparing the same, and a pharmaceutical composition containing the compound as an active ingredient. More particularly, invention relates to a novel thiazolidine derivative of the formula:

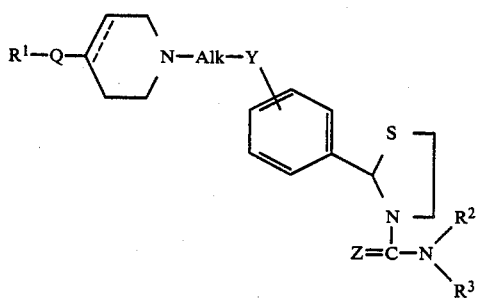

wherein $R^1$ is a substituted or unsubstituted phenyl group, $R^2$ is hydrogen or a lower alkyl group, $R^3$ is hydrogen, a lower alkyl group or a lower alkanoyl group, Q is a single bond or a lower alkylene group, Alk is a lower alkylene group, Y and Z are the same or different and are an oxygen atom or a sulfur atom and the group of the formula:

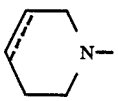

is either

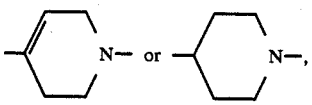

or a pharmaceutically acceptable salt thereof.

In the present specification, the term "lower alkyl" denotes a straight or branched alkyl having 1 to 5 carbon atoms, and the term "lower alkylene" denotes a straight or branched alkylene having 1 to 5 carbon atoms. The term "lower alkanoyl" denotes a straight or branched alkanoyl having 2 to 6 carbon atoms, and the term "lower alkanoic acid" denotes a stright or branched alkanoic acid having 2 to 6 carbon atoms. The term "lower alkoxy" denotes a straight or branched alkoxy having 1 to 5 carbon atoms.

The compound (I) of the present invention and a salt thereof are novel and useful as cardiotonic agents. For example, N-methyl-2-{2-[3-(4-phenyl-1,2,3,6-tetrahydropyridin-1-yl)propoxy]phenyl}thiazolidine-3-carbothioamide hydrochloride when administered intravenously to dogs at a dose of 0.03 mg/kg shows approximately a 34% increase in left ventricular contractility, and the cardiotonic effect of the compound of the present invention lasts for about 30 minutes. Moreover, when examined by the use of isolated heart of guinea pig (Langendorff's method), N-methyl-2-{2-[2-(4-phenyl-1,2,3,6-tetrahydropyridin-1-yl)ethyloxy]phenyl} thiazolidine-3-carbothioamide hydrochloride at a dose of 10 μg shows an increase in cardiac contractile force.

Examples of the compounds of the present invention are those of the formula (I) in which $R^1$ is a phenyl group which is unsubstituted or substituted with a halogen atom (e.g., fluorine, chlorine or bromine), lower alkyl (e.g., methyl, ethyl, propyl, butyl or pentyl) or lower alkoxy (e.g., methoxy, ethoxy, propoxy, butoxy or pentyloxy); $R^2$ is hydrogen or lower alkyl (e.g., methyl, ethyl, propyl, butyl or pentyl); $R^3$ is hydrogen, lower alkyl (e.g., methyl, ethyl, propyl, butyl or pentyl) or lower alkanoyl (e.g., acetyl, propionyl, butyryl, valeryl or hexanoyl); the group Q is a single bond or lower alkylene (e.g., methylene, ethylene, trimethylene, tetramethylene or pentamethylene); Alk is lower alkylene (e.g., methylene, ethylene, trimethylene, tetramethylene or pentamethylene); Y and Z are the same or different and are an oxygen atom or a sulfur atom; and the group of the formula:

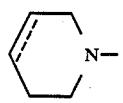

is either

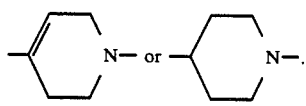

Preferred compounds are those of the formula (I) in which $R^1$ is phenyl which is unsubstituted or substituted with fluorine, methyl or methoxy; $R^2$ is hydrogen or methyl; $R^3$ is hydrogen, methyl, ethyl, butyl or acetyl; Q is a single bond or methylene; Alk is ethylene or trimethylene; Y and Z are the same or different and are an oxygen atom or a sulfur atom; and the group of the formula:

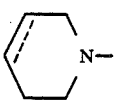

is either

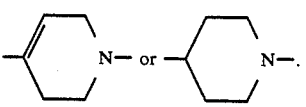

other preferred compounds are those of the formula (I) in which $R^1$ is phenyl, 3-fluorophenyl, 3-methylphenyl, 3-methoxyphenyl or 4-methoxyphenyl, $R^2$ is hydrogen or methyl, $R^3$ is hydrogen, methyl, ethyl, butyl or acetyl, Q is a single bond or methylene, Alk is ethylene or trimethylene, Y and Z are the same or different and are an oxygen atom or a sulfur atom, and the group or the formula:

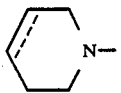

is either

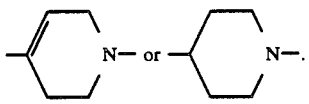

In the formula (I) it is preferred that, when the carbon atom of the benzene ring which carries a thiazolidine group is taken as the 1-position, the substituent:

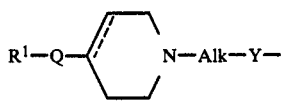

is substituted at the 2- or 4-position of the benzene ring thereof. Other preferred compounds are those of the formula:

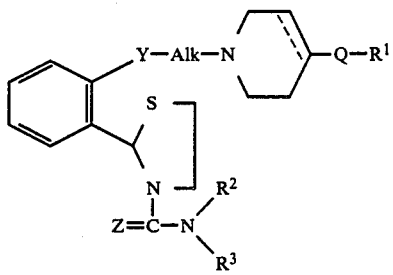
(I-A)

wherein $R^1$ is a substituted or unsubstituted phenyl group, $R^2$ is hydrogen or a lower alkyl group, $R^3$ is hydrogen, a lower alkyl group or a lower alkanoyl group, Q is a single bond or a lower alkylene group, Alk is a lower alkylene group, Y and Z are the same or different and are an oxygen atom or a sulfur atom and the group of the formula:

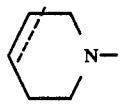

is either

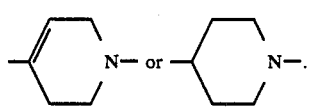

Other preferred compounds are those of the formula (I-A) in which $R^1$ is a phenyl group which is unsubstituted or substituted with a halogen atom, a lower alkyl group or a lower alkoxy group, $R^2$ is hydrogen or a lower alkyl group, $R^3$ is hydrogen, a lower alkyl group or a lower alkanoyl group, Q is a single bond or a lower alkylene group, Alk is a lower alkylene group, Y and Z are the same or different and are an oxygen atom or a sulfur atom and the group of the formula:

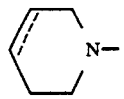

is either

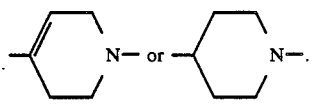

Still other preferred compounds are those of the formula (I-A) in which $R^1$ is phenyl which is unsubstituted or substituted with fluorine, methyl or methoxy, $R^2$ is hydrogen or methyl, $R^3$ is hydrogen, methyl, ethyl, butyl or acetyl, Q is a single bond or methylene, Alk is ethylene or trimethylene, Y and Z are the same or different and are an oxygen atom or a sulfur atom and the group of the formula:

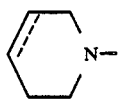

is either

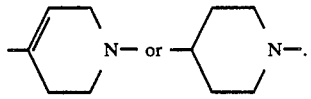

Further preferred compounds are those of the formula (I-A) in which $R^1$ is phenyl which is unsubstituted or substituted with a halogen atom, a lower alkyl group or a lower alkoxy group, $R^2$ is hydrogen, $R^3$ is a lower alkyl group, Q is a single bond, Alk is a lower alkylene group, Q is a single bond, Alk is lower alkylene group, Y is an oxygen atom, Z is an oxygen atom or a sulfur atom and the group of the formula:

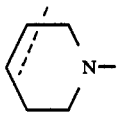

is either

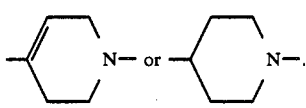

Still further preferred compounds are those of the formula (I-A) in which $R^1$ is phenyl, fluorophenyl, methylphenyl or methoxyphenyl, $R^2$ is hydrogen, $R^3$ is methyl, ethyl or butyl, Alk is ethylene or trimethylene, Q is a single bond, Y is an oxygen atom, Z is an oxygen atom or a sulfur atom and the group of the formula:

is either

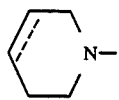

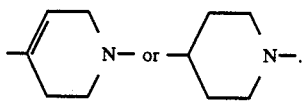

Particularly preferred compounds are those of the formula (I-A) in which $R^1$ is phenyl, 3-fluorophenyl, 3-methylphenyl, 3-methoxyphenyl or 4-methoxyphenyl, $R^2$ is hydrogen, $R^3$ is methyl, Alk is ethylene, Q is a single bond, Y is an oxygen atom, Z is an oxygen atom or a sulfur atom and the group of the formula:

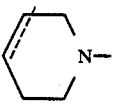

is either

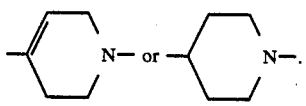

The compound of the formula (I) has an asymmetric carbon at the 2-position of the thiazolidine ring and can exist in the form of two optical isomers. The present invention includes within its scope either one of these isomers and a racemic modification thereof.

The compound (I) of the present invention can be prepared, for example, by the steps of:

[Process (A)] reacting a thiazolidine derivative of the formula:

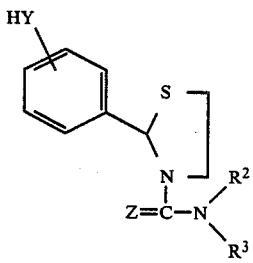 (II)

wherein $R^2$, $R^3$, Y and Z are the same as defined above, or a salt thereof with a compound of the formula:

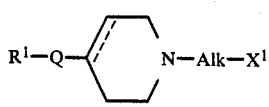 (III)

wherein $X^1$ is a reactive residue, and $R^1$, Q, Alk and the group:

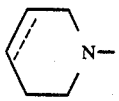

are the same as defined above, or a salt thereof; or

[Process (B)] reacting a thiazolidine derivative of the formula:

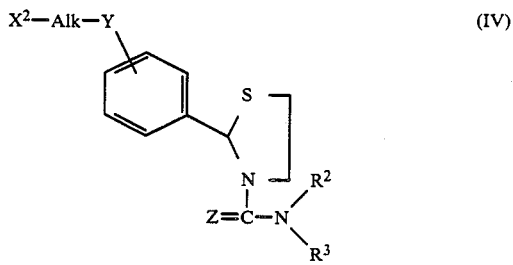 (IV)

wherein $X^2$ is a reactive residue, and Alk, $R^2$, $R^3$, Y and Z are the same as defined above, or a salt thereof with a compound of the formula:

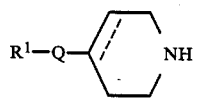 (V)

wherein $R^1$, Q and the group:

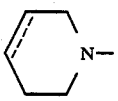

are the same as defined above, or a salt thereof; or

[Process (C)] reacting a thiazolidine derivative of the formula:

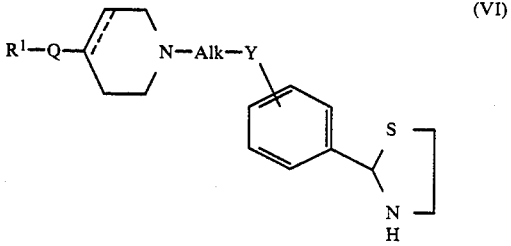 (VI)

wherein $R^1$, Q, Y, Alk and the group:

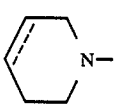

are the same as defined above, or a salt thereof with a compound of the formula:

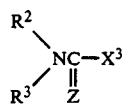
(VII)

wherein $X^3$ is a reactive residue, and $R^2$, $R^3$ and Z are the same as defined above; or

[Process (D)] reacting a thiazolidine derivative of the formula

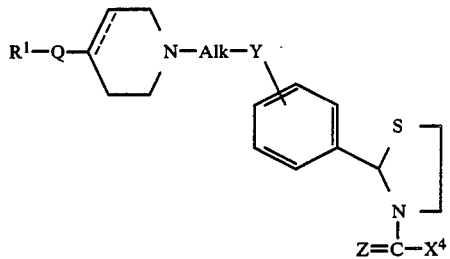
(VIII)

wherein $X^4$ is a reactive residue, and $R^1$, Q, Alk, Y, Z and the group:

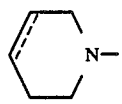

are the same as defined above, or a salt thereof with an amine compound of the formula:

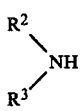
(IX)

wherein $R^2$ and $R^3$ are the same as defined above, or a salt thereof.

Alternatively, the compound (I) in which Z is an oxygen atom [i.e., a thiazolidine derivative (I-a)] may be prepared by the step of:

[Process (E)] reacting a thiazolidine derivative of the formula:

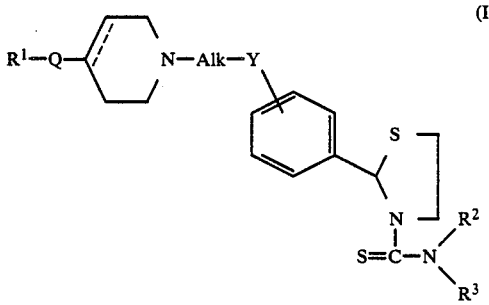
(I-b)

wherein $R^1$, $R^2$, $R^3$, Q, Y, Alk and the group:

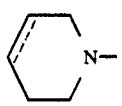

are the same as defined above, or a salt thereof with a glycidic compound of the formula:

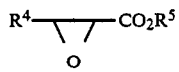
(X)

wherein $R^4$ is a lower alkyl group or a substituted or unsubstituted phenyl group and $R^5$ is a lower alkyl group.

The compound (I) in which $R^2$ is a hydrogen atom [i.e., a thiazolidine derivative (I-c)] may be prepared, for example, by the step of:

[Process (F)] reacting the thiazolidine derivative (VI) or a salt thereof with a compound of the formula:

$$R^3-NC=Z \qquad (XI)$$

wherein $R^3$ and Z are the same as defined above.

The starting compounds (II), (III), (IV), (V), (VI), (VIII) and (XI) may be used either in a free form or in the form of a salt thereof. Any conventional acid addition salts such as hydrochloride, hydrobromide, sulfate, nitrate and so forth may be used as the salts of the compounds (III), (V), (VI), (VIII) and (IX). Alkali metal salts such as sodium salt or potassium salt or organic amine salts may be used as the salts of the compounds (II) and (IV). Moreover, the compound (I-b) of the present invention may be used in the above mentioned-reaction either in free form or in the form of salts thereof such as, for example, hydrochloride, hydrobromide, sulfate, nitrate, sodium salt, potassium salt and so forth. Further, examples of the starting compounds (III), (IV), (VII) and (VIII) include those in which the reactive residue defined for each one of the groups $X^1$, $X^2$, $X^3$ and $X^4$ is a halogen atom such as chlorine or bromine, a substituted or unsubstituted phenylsulfonyloxy group such as tosyloxy group or a lower alkylsulfonyloxy group such as methanesulfonyloxy group.

(Processes A, B, C and D)

All these reactions can be accomplished in the presence or absence of an acid acceptor in a solvent. Examples of the acid acceptor which may be used in these reactions include inorganic bases such as potassium hydroxide, sodium hydroxide, potassium carbonate, sodium carbonate, potassium bicarbonate or sodium bicarbonate, organic bases such as triethylamine, N-methylmorpholine, pyridine or diisopropylethylamine, and the like. Dimethylformamide, dimethylsulfoxide, acetonitrile, dioxane, tetrahydrofuran, acetone, methanol and ethanol are suitable as the reaction solvent for Processes (A) and (B), and tetrahydrofuran, dioxane, pyridine and dimethylformamide are suitable as the solvent for Process (C). On the other hand, examples of suitable solvents for Process (D) are tetrahydrofuran, toluene, acetonitrile and dioxane. It is preferred to carry out Processes (A) and (B) at about 50° to 110° C., especially at about 60° to 100° C. It is also preferred to carry out Process (C) at about 0° to 80° C., especially at about 25° to 60° C., and to carry out Process (D) at about 0° C., especially at about 10° to 50° C.

(Process E)

The reaction of the thiazolidine derivative (I-b) or a salt thereof with the glycidic compound (X) can be carried out in a solvent. Examples of the group represented by $R^4$ are a lower alkyl group such as methyl, ethyl, propyl or butyl, and a substituted or unsubstituted phenyl group such as phenyl, methylphenyl, methoxyphenyl or ethoxphenyl. On the other hand, examples of the group represented by $R^5$ are a lower alkyl group such as methyl, ethyl, propyl or butyl. The glycidic compound (X) may exist in the form of the cis- or trans-isomer, and either one of these isomers may be used in the reaction. Lower alkanols such as methanol, ethanol or propanol, tetrahydrofuran, dioxane and benzene are suitable as the solvent. The reaction temperature is preferably in the range of about 40° to 100° C., more preferably in the range of about 60° to 80° C.

(Process F)

The condensation reaction of the compound (VI) or its salt and the compound (XI) can be carried out in a solvent. Examples of the solvent are methanol, ethanol, tetrahydrofuran, dioxane or acetonitrile. It is preferred to carry out the reaction at a temperature of about 25° to 100° C., especially at about 60° to 80° C. Alternatively, when $R^3$ is hydrogen, the compound (I-c) may be prepared by reacting the compound (VI) with an alkali metal salt of the compound (XI) ($R^3$=hydrogen) such as potassium isocyanate, sodium isocyanate, potassium isothiocyanate or sodium isothiocyanate in the presence of an acid (e.g., acetic acid, hydrochloric acid or sulfuric acid) in a solvent, since the compound (XI) in which $R^3$ is hydrogen is prepared from the alkali metal salt of the compound (XI) and the acid. Examples of the solvent are water, tetrahydrofuran, dioxane, lower alkanol (e.g., methanol, ethanol, propanol) or a mixture thereof. It is preferred to carry out the reaction at a temperature of about 0° to 60° C., especially at about 10° to 25° C.

If the compound (I) thus obtained is a racemic modification, it may be resolved into each optical isomer thereof. For example, the racemic modification of the compound (I) in which $R^2$ is lower alkyl and $R^3$ is hydrogen atom may be resolved into each optical isomer thereof by the steps of reacting the compound with an optically active 1-(2-naphthylsulfonyl)pyrrolidine-2-carbonyl halide to give a pair of diastereoisomers, separating the diastereoisomers from each other by selective crystallization or by column chromatography, and hydrolyzing each diastereoisomer.

The starting compounds (II), (IV), (VI) and (VIII) are novel compounds. Among them, the starting compound (II) may be prepared, for example, by reacting a compound of the formula:

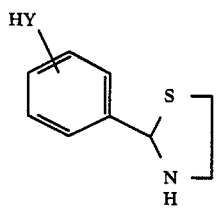

(XII)

wherein Y is the same as defined above, with the compound (VII) in the same manner as described in Process (C). Alternatively, the compound (II) may be prepared by reacting the compound (XII) with the compound (XI) in the same manner as described in Process (F) to give a compound of the formula:

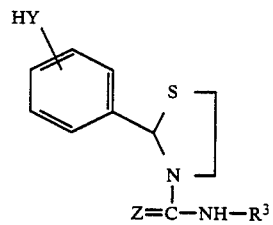

(XIII)

wherein $R^3$, Y and Z are the same as defined above, and when $R^3$ is a lower alkyl group, optionally reacting the thus obtained product or a salt thereof with a comound of the formula:

$R^{31}X^5$ (XIV)

wherein $R^{31}$ is a lower alkyl group or a lower alkanoyl group and $X^5$ is a reactive residue such as those described in the case of $X^1$ to $X^4$. When $R^{31}$ is a lower alkanoyl group, an example of the compound (XIV) also includes a lower alkanoic acid anhydride. This optional reaction may be carried out in a conventional manner. For instance, the reaction of the compound (XIII) with the compound (XIV) ($X^5$=OH) may be carried out in the presence of a dehydration agent (e.g., carbonyldiimidazole or dicyclohexylcarbodiimide) in a solvent. On the other hand, the reaction of the compound (XIII) with the compound (XIV) ($X^5$=halogen atom, a substituted or unsubstituted phenylsulfonyloxygroup, or a lower alkylsulfonyloxy group) or with the lower alkanoic acid anhydride may be carried out in a solvent in the absence or presence of an acid acceptor such as those described in Processes (A) to (D). Examples of the solvent are tetrahydrofuran, dioxane, benzene and toluene. The reaction may be carried out at a temperature of 0° to 80° C., preferably at 24° to 60° C.

The compound (IV) may be prepared by reacting the compound (II) with a compound of the formula:

$X^2$-Alk-$X^6$ (XV)

wherein $X^6$ is a reactive residue such as a halogen atom, a substituted or unsubstituted phenylsulfonyloxy group or a lower alkylsulfonyloxy group, and Alk and $X^2$ are the same as defined above, at 0° to 100° C. in the presence of an acid acceptor such as those described in Processes (A) to (D).

The compound (IV) may also be prepared by reacting a compound of the formula:

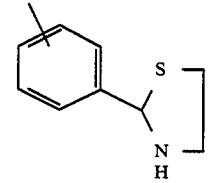

(XVI)

wherein Alk, Y and $X^2$ are the same as defined above, with the compound (VII) in the same manner as described in Process (C). Alternatively, the compound (IV) may be prepared by reacting the compound (XVI) with the compound (XI) in the same manner as described in Process (F) to give a compound of the formula:

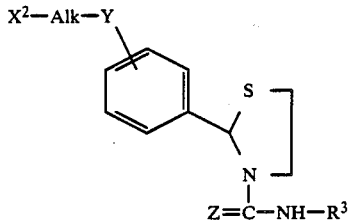

(XVII)

wherein $R^3$, Alk, Y, Z and $X^2$ are the same as defined above, and when $R^3$ is a lower alkyl group, optionally reacting the thus-obtained product with the compound (XIV) in the same manner as described in the reaction of the compound (XIII) and (XIV). The compound (VI) may be prepared by condensing a compound of the formula:

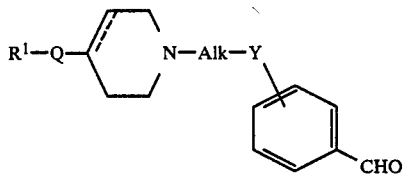

(XVIII)

wherein $R^1$, Q, Alk, Y and the group:

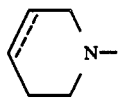

are the same as defined above, with cysteamine or a salt thereof at 25° to 100° C. in the absence or presence of an acid acceptor such as those described in Processes (A) to (D). The reaction of the compound (VI) or a salt thereof with a compound of the formula: $Z=C-(X^4)_2$ (XIX) ($X^4$ and Z: same as defined above) gives the compound (VIII). These reactions may be carried out at a temperature of 0° to 80° C. in the absence or presence of an acid acceptor such as those described in Processes (A) to (D).

The compounds (II), (IV), (VI), (VIII) and (I-b) obtained above may be used in the subsequent step or steps without isolation and/or purification from the reaction mixture.

The compound (I) of the present invention can be used as a medicine in a free form or a pharmaceutically acceptable salt thereof. Any pharmaceutically acceptable salts of the compound (I) may be used for this purpose, and such salts include, for example, inorganic acid addition salts (e.g., hydrochloride, sulfate, nitrate, phosphate or hydrobromide), organic acid addition salts (e.g., acetate, oxalate, fumarate, succinate, maleate, citrate, lactate, glucuronate, pyruvate, tartrate, benzenesulfonate, sulfamate, or methanesulfonate) and alkali metal salts (e.g., sodium or potassium salt). These salts may easily be prepared by treating a free form of the compound (I) with an acid or an alkali agent in the usual manner.

The compound (I) of the present invention and a salt thereof have a potent and long-lasting cardiotonic effect, and are useful for the treatment or prophylaxis of congestive heart failure. For example, the compound (I) and a salt thereof are useful for the treatment, prophylaxis and/or amelioration of various symptoms such as, for example, edema, dyspnea, cyanosis and hypoxia which are usually observed in patients with heart failure.

Moreover, the compound (I) of the present invention and a salt thereof show long-lasting positive inotropic effects by oral administration and is especially characterized by its small side effects (e.g., the effect on heart rate).

The compound (I) of the present invention and pharmaceutically acceptable salts thereof can be administered by either oral or parenteral routes. However, as they show excellent cardiotonic activity even by oral administration, they are particularly suitable for use by the oral route. For oral administration, the compound of the present invention and a salt thereof may be used in the form of conventional preparations, e.g., tablets, powders, capsules or granules, which may contain conventional carriers, e.g., calcium carbonate, calcium phosphate, corn starch, potato starch, sucrose, lactose, talc or magnesium stearate. They may also be used in liquid preparations, e.g., aqueous or oily suspensions, solutions, syrups or elixirs. For parenteral administration, the compound of the present invention and a salt therof may be used, for example, in the form of an injection preparation or suppository. The injection preparation may be in the form of a solution or a suspension which may contain distilled water, an essential oil (e.g., peanut oil or corn oil) or hydrophobic solvent (e.g., polyethylene glycol, polypropylene glycol, lanoline or coconut oil). These preparations may be sterilized and further may contain for example other conventional additives, e.g. preservatives or stabilizers.

The dose of the compound (I) of the present invention or a salt thereof may vary according to the administration route, the age, body weight and condition of the patient and the kind and severity of the disease, but is preferably in the range of 0.01 to 100 mg/kg/day, more preferably 0.03 to 50 mg/kg/day.

Practical and presently-preferred embodiments of the present invention are illustratively shown by the following Experiments and Examples, but should not be construed to be limited thereto.

Experiment 1

Method: Male mongrel dogs weighing 10 to 20 kg were anesthetized with sodium pentobarbital (30 mg/kg, i.v.). Thoracotomy was performed at the left fourth intercostal space. Left ventricular pressure was measured by a small pressure transducer (Konigsberg) inserted into the left ventricle. Cardiotonic activity of a test compound was assessed by an increase in the first derivative of left ventricular pressure. Drugs were given intravenously in a dose of 0.03 mg/kg.

Results: The results are shown in Table 1.

TABLE 1

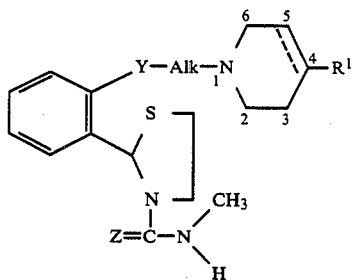

| Test compound | | | | | Cardiotonic activity | |
|---|---|---|---|---|---|---|
| $R^1$ | Alk | Y | Z | 4–5* Bond | Increase (%) in left ventricular contractility | Duration of action (minute) |
| phenyl | —(CH$_2$)$_3$— | O | S | d | 34 | 30 |
| 3-methoxyphenyl | —(CH$_2$)$_2$— | O | S | d | 30 | 35 |
| phenyl | " | O | O | d | 31 | 32 |
| 3-fluorophenyl | " | O | S | s | 22 | 25 |

Note:
*"d" and "s" mean double bond and single bond, respectively;

between 4 and 5-positions of the group: —N⟨⟩.

Experiment 2

Method: The isolated hearts of guinea pigs (weighing: about 230 g) were perfused with the Langendorff's method. Locke-Ringer's solution containing 2% of defibrinated rabbit blood was used as a perfusing solution (at 30° C.). Contractile force was measured by means of a strain gauge transducer. Drugs were administered into an aortic cannula.

Results: The results are shown in Table 2.

TABLE 2

| Test compound | | | | Cardiotonic activity |
|---|---|---|---|---|
| $R^1$ | Y | Z | 4–5* Bond | Minimum effective dose** (μg/heart) |
| phenyl | O | S | d | 10 |

TABLE 2-continued

[Structure: benzene ring with Y—(CH₂)₂—N(piperidine-R¹) substituent, and thiazolidine ring with Z=C—N(CH₃)H]

| Test compound | | | | Cardiotonic activity |
|---|---|---|---|---|
| R¹ | Y | Z | 4-5* Bond | Minimum effective dose** (μg/heart) |
| 3-F-phenyl | O | S | s | 10 |
| 3-F-phenyl | O | O | d | 10 |
| 3-F-phenyl | O | S | d | 10 |

Note;
*The same as defined in the footnote of Table 1.
**The minimum effective dose means a minimum amount which is necessary to produce an increase in cardiac contractile force of the isolated guinea pig's heart.

EXAMPLE 1

A mixture of 1.27 g of N-methyl-2-(2-hydroxyphenyl)thiazolidine-3-carbothioamide, 1.38 g of 1-(2-chloroethyl)-4-(3-fluorophenyl)-1,2,3,6-tetrahydropyridine hydrochloride, 1.50 g of potassium carbonate, 0.75 g sodium iodide and 25 ml of dimethylformamide is stirred at 90° C. for 8 hours. 0.7 g of 1-(2-chloroethyl)-4-(3-fluorophenyl)-1,2,3,6-tetrahydropyridine hydrochloride is added to the reaction mixture, and the mixture is further stirred at the same temperature for 15 hours. The mixture is evaporated under reduced pressure to remove the solvent. Water is added to the residue, and the aqueous solution is extracted with ethyl acetate. The extract is washed with water, dried and then evaporated to remove the solvent. The residue is purified by silica gel column chromatography (solvent, chloroform:ethanol=45:1), whereby 0.39 g of N-methyl-2-{2-[2-(4-(3-fluorophenyl)-1,2,3,6-tetrahydropyridin-1-yl)ethyloxy]phenyl}thiazolidine-3-carbothioamide is obtained.

m.p. 147°–148.5° C. (recrystallized from a mixture of ethyl acetate and n-hexane).

Oxalate:
m.p. 155°–159° C. (decomp., recrystallized from a mixture of methanol and ether).

EXAMPLES 2 TO 7

The following compounds are obtained from the corresponding starting compounds in the same manner as described in Example (1).

TABLE 3

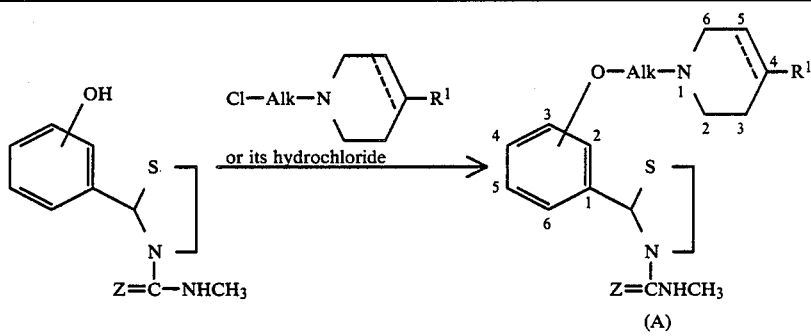

| Example Nos. | R¹ | Z | Alk | 4-5 Bond* | Position** | Properties |
|---|---|---|---|---|---|---|
| 2 | 3-OCH₃-phenyl | S | (CH₂)₂ | d | 2 | Free base: m.p. 149–152° C. (recrystallized from ethanol-ether) Oxalate.½H₂O: m.p. 151–152° C. (decomp., recrystallized from ethanol) |
| 3 | phenyl | S | (CH₂)₂ | d | 2 | Free base: m.p. 140–146° C. Hydrochloride: m.p. 208–212.5° C. (decomp., recrystallized from methanol-ethanol-ether) |

TABLE 3-continued

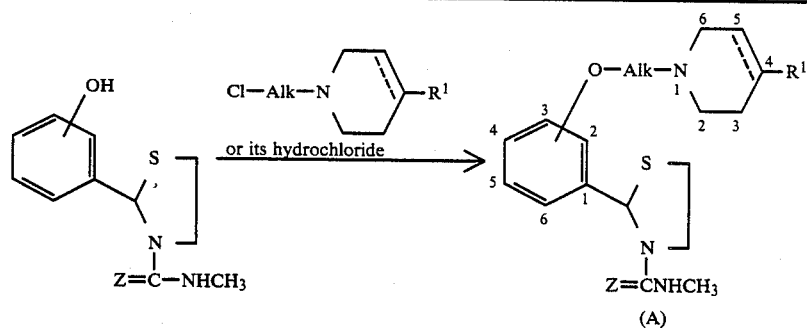

| Example Nos. | R¹ | Z | Alk | 4-5 Bond* | Position** | Properties |
|---|---|---|---|---|---|---|
| 4 | (3-F-phenyl) | O | (CH₂)₂ | s | 2 | Free base: m.p. 195–198° C. (recrystallized from ethanol) Oxalate: m.p. 168–170° C. (decomp.) |
| 5 | (3-OCH₃-phenyl) | O | (CH₂)₂ | s | 2 | Free base: m.p. 130–132.5° C. (washed with ether) Oxalata: m.p. 142.5–144.5° C. (decomp., recrystallized from acetone) |
| 6 | phenyl | O | (CH₂)₃ | s | 2 | Free base: Yield: 63.2%, m.p. 113–115.5° C. (recrystallized from ethyl acetate-isopropyl ether) Oxalate.½H₂O: m.p. 113–117° C. (decomp., recrystallized from ethanol-acetone-ether) |
| 7 | phenyl | O | (CH₂)₂ | d | 4 | Free base: oil IR $\nu^{liq}_{max}$ (cm$^{-1}$): 3400, 3300, 1620 Mass (m/e): 423(M⁺), 366, 322, 184, 172 Oxalate.½EtOH: m.p. 120–121° C. (decomp., recrystallized from ethanol) |

Note;
*The same as defined in the footnote of Table 1.
**Position means the position of the group:

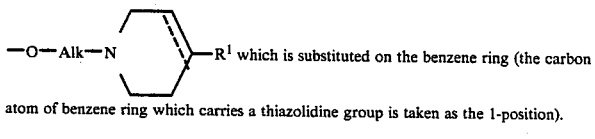

R¹ which is substituted on the benzene ring (the carbon atom of benzene ring which carries a thiazolidine group is taken as the 1-position).

EXAMPLE 8

A mixture f 2.25 g of N-methyl-2-[2-(2-chloroethylthio)phenyl]thiazolidine-3-carboxamide, 1.3 g of 4-phenylpiperidine, 1.18 g of sodium iodide, 2.16 g of potassium carbonate and 25 ml of dimethylformamide is stirred at 80° C. for 20 hours. Water is added to the reaction mixture and the mixture is extracted with chloroform. The extract is washed with water, dried and then evaporated to remove the solvent. The residue is purified by silica gel column chromatography (solvent, chloroform:methanol=40:1) and washed with ether, whereby 2.37 g of N-methyl-2-{2-[2-(4-phenylpiperidin-1-yl)ethylthio]phenyl}thiazolidine-3-carboxamide are obtained.
Yield: 76.7%.
m.p. 169°–172° C.

Oxalate.½H₂O.½C₂H₅OH;
m.p. 145°–148° C. (decomp.) (recrystallized from a mixture of ethanol and ether).

EXAMPLES 9 TO 13

The following comounds are obtained from the corresponding starting compounds in the same manner as described in Example 8.

TABLE 4

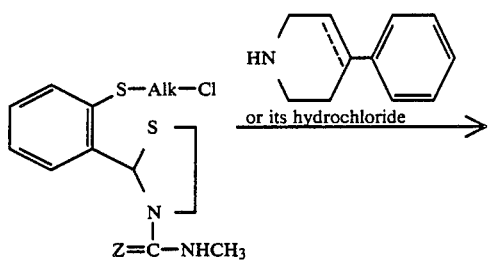

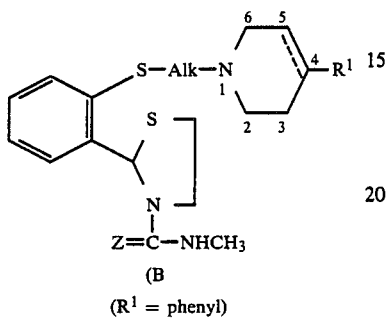

(B ($R^1$ = phenyl)

| Example Nos. | Compound (B) | | 4-5 Bond* | Properties |
|---|---|---|---|---|
| | Z | Alk | | |
| 9 | O | $(CH_2)_2$ | d | Free base:<br>m.p. 129–131° C.<br>(recrystallized from ethanol-ether)<br>Oxalate.½EtOH:<br>m.p. 127–132° C. (recrystallized from ethanol-ether) |
| 10 | S | $(CH_2)_3$ | s | Free base:<br>Yield: 73.9%, m.p. 133–137° C.<br>(Washed with ether)<br>Oxalate:<br>m.p. 137–140° C. (decomp., recrystallized from ethanol-ether) |
| 11 | S | $(CH_2)_3$ | d | Free base:<br>Yield: 62%, m.p. 114–118° C.<br>(washed with ether)<br>Oxalate:<br>m.p. 132–134° C. (decomp., recrystallized from ethanol-ether) |
| 12 | O | $(CH_2)_3$ | s | Free base:<br>Yield: 61.5%, m.p. 142–144° C.<br>(washed with ether)<br>Fumarate.½$H_2O$:<br>m.p. 139–141° C. (decomp., recrystallized from ether) |
| 13 | O | $(CH_2)_3$ | d | Free base:<br>m.p. 87–90° C.<br>(washed with ether)<br>Oxalate.½$H_2O$:<br>m.p. 116–132° C. (decomp., recrystallized from ethanol-ether) |

Note;
*the same as defined in the footnote of table 1.

EXAMPLE 14

A mixture of 2.4 of N-methyl-2-[2-(2-chloroethylthio)phenyl]thiazolidine-3-carbothioamide, 1.34 g of 4-phenylpiperidine, 1.22 g of sodium iodide, 2.16 g of potassium carbonate and 25 ml of dimethylformamide is stirred at 80° C. for 10 hours. The mixture is poured into ice-water, and the aqueous mixture is extracted with chloroform. The extract is washed with water, dried and then purified by silica gel column chromatography (solvent, chloroform:ethanol=50:1), whereby 1.15 g of N-methyl-2-{2-[2-(4-phenylpiperidin-1-yl)ethylthio]phenyl}thiazolidine-3-carbothioamide are obtained.

m.p. 124°–127° C.

Oxalate.½$C_2H_5OH$:

m.p. 138°–139° C. (decomp., recrystallized from ethanol).

EXAMPLES 15 TO 27

The follwing compounds (C) and (D) are obtained from the corresponding starting compounds in the same manner as described in Example 14.

TABLE 5

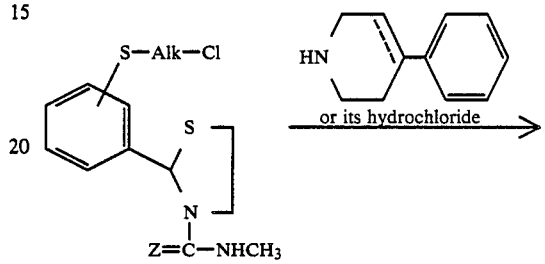

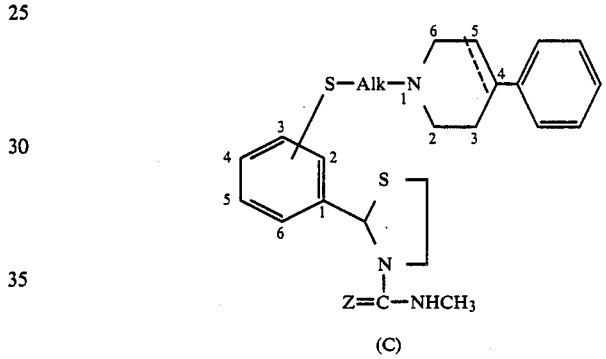

(C)

| Example Nos. | Compound (C) | | | | Properties |
|---|---|---|---|---|---|
| | Z | Alk | 4-5* Bond | Position** | |
| 15 | S | $(CH_2)_2$ | d | 2 | Free base:<br>Yield: 50.6%,<br>m.p. 126–134° C.<br>Oxalate.½$(C_2H_5)_2O$:<br>m.p. 137–165° C. (decomp., recrystallized from ethanol-ether) |
| 16 | S | $(CH_2)_3$ | s | 4 | Free base:<br>Yield: 89%,<br>m.p. 131–132.5° C.<br>(recrystallized from ethyl acetate-isopropyl ether)<br>Oxalate:<br>m.p. 180–181° C. (decomp., recrystallized from aqueous methanol) |
| 17 | O | $(CH_2)_2$ | s | 4 | Free base:<br>Yield: 63%, oil<br>Oxalate:<br>m.p. 163–165° C.<br>(recrystallized from ethanol) |
| 18 | S | $(CH_2)_2$ | s | 4 | Free base:<br>oil<br>Oxalate:<br>m.p. 162–164° C. (decomp., recrystallized from methanol-ethanol) |
| 19 | O | $(CH_2)_3$ | s | 4 | Free base:<br>Yield: 66%,<br>m.p. 103–118° C.<br>(recrystallized from isopropyl ether-ethanol) |

TABLE 5-continued

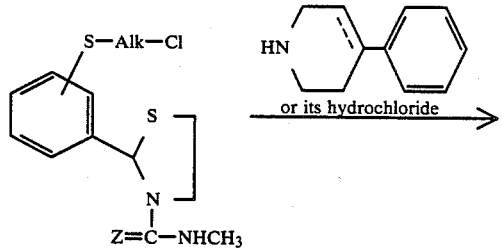

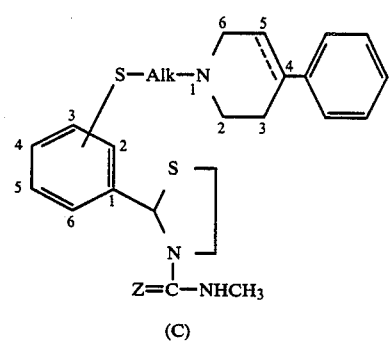

(C)

| | | Compound (C) | | |
|---|---|---|---|---|
| Example Nos. | Z | Alk | 4-5* Bond | Posi- tion** | Properties |

Oxalate.½H₂O:

m.p. 77–81° C.

(recrystallized from ethanol)

Note;

*The same as defined in the footnote of Table 1.

**Position means the position of the group:

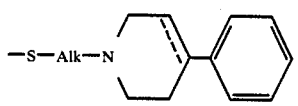

which is substituted on the benzene ring (the carbon atom of benzene ring which carries a thiazolidine group is taken as the 1-position).

TABLE 6

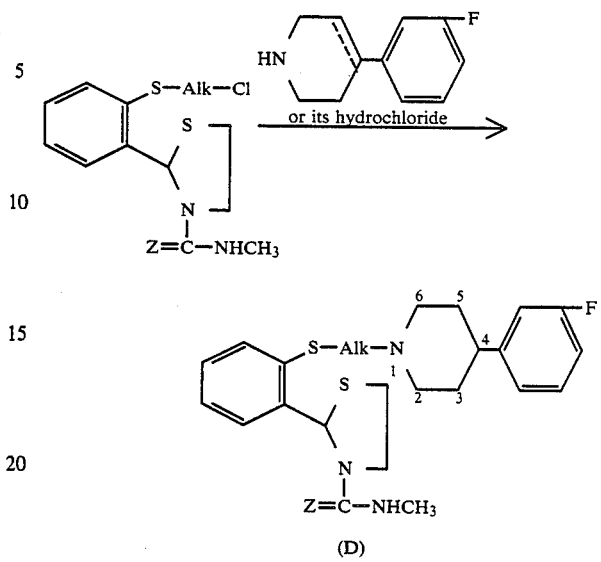

(D)

| Example Nos. | Compound (D) Z | Alk | 4-5* Bond | Properties |
|---|---|---|---|---|
| 20 | O | (CH₂)₂ | s | Free base: Yield: 66%, m.p. 174–175° C. (recrystallized from ethyl acetate-ether) Oxalate: m.p. 115–117° C. (recrystallized from ethanol-ether) |
| 21 | O | (CH₂)₂ | d | Free base: Yield: 56%, m.p. 152–154° C. (recrystallized from ethyl acetate-ether) Oxalate: m.p. 143–144° C. (decomp., recrystallized from ethanol) |
| 22 | O | (CH₂)₃ | s | Free base: Yield: 83%, m.p. 148–149° C. (recrystallized from ethyl acetate-ether) Oxalate.¼H₂O: m.p. 97–99° C. (recrystallized from ethanol-ether) |
| 23 | O | (CH₂)₃ | d | Free base: Yield: 59.6%, m.p. 119.5–122° C. (recrystallized from ethyl acetate-n-hexane) Oxalate: m.p. 137.5–140° C. (decomp. recrystallized from acetone) |
| 24 | S | (CH₂)₂ | s | Free base: m.p. 151–153° C. (recrystallized from ethyl acetate-ether) Oxalate.½H₂O: m.p. 135–136° C. (decomp., recrystallized from ethanol) |
| 25 | S | (CH₂)₂ | d | Free base: oil Oxalate: m.p. 158–160° C. (decomp., recrystallized from ethanol) |
| 26 | S | (CH₂)₃ | s | Free base: Yield: 62.4%, m.p. 128–133° C. (recrystallized from ethyl acetate-n-hexane) Oxalate: m.p. 140–144° C. (decomp., recrystallized from ethanol-methanol-ether) |
| 27 | S | (CH₂)₃ | d | Free base: m.p. 136–141° C. (recrystallized from ethyl acetate) Oxalate: m.p. 135–138° C. (decomp., |

TABLE 6-continued

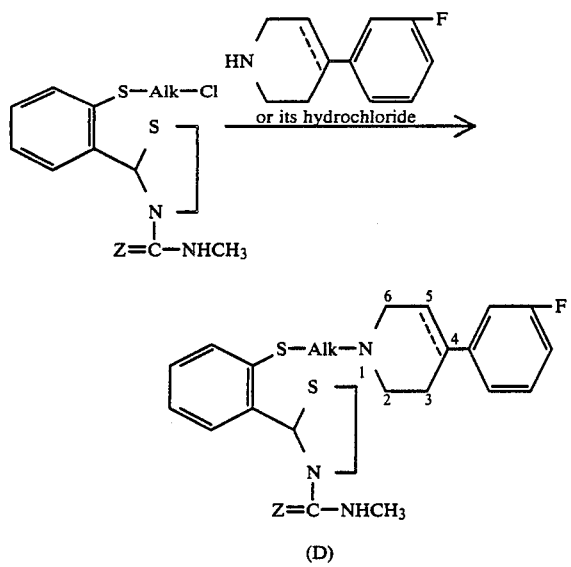

| Example Nos. | Compound (D) Z | Alk | 4-5* Bond | Properties |
|---|---|---|---|---|
| | | | | recrystallized from acetone) |

Note;
*The same as defined in the footnote of Table 1.

EXAMPLE 28

A mixture of 2.22 g of N-methyl-2-[2-(2-chloroethyloxy)phenyl]thiazolidine-3-carbothioamide, 1.58 g of 4-(3-methoxyphenyl)1,2,3,6-tetrahydropyridine hydrochloride, 1.93 g of potassium carbonate, 1.05 g of sodium iodide, and 20 ml of dimethylformamide is stirred at 70° to 80° C. for 21 hours. The mixture is evaporated to remove the solvent. Water is added to the residue, and the aqueous solution is extracted with ethyl acetate. The extract is washed with a saturated sodium chloride solution, dried, and then evaporated to remove the solvent. The residue is purified by silica gel column chromatography (solvent, chloroform:ethyl acetate=3:1), whereby 1.14 g of N-methyl-2-{2-[2-(4-(3-methoxyphenyl)-1,2,3,6-tetrahydropyridin-1-yl)ethyloxy]phenyl}thiazolidine-3-carbothioamide are obtained.

m.p. 149°–152° C. (recrystallized from a mixture of ethanol and ether).

Oxalate.½H$_2$O:

m.p. 151°–152° C. (decomp., recrystallized from ethanol).

EXAMPLES 29 TO 52

The following compounds are obtained from the corresponding starting compounds in the same manner as described in Example 28.

TABLE 7

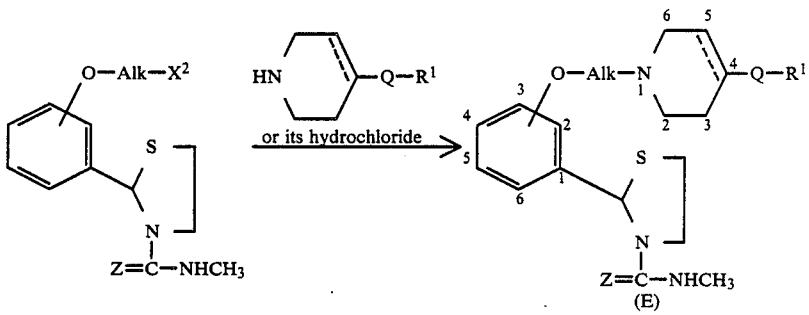

| Example Nos. | Compound (E) Q—R$^1$ | Z | Alk | 4-5* Bond | position** | Properties |
|---|---|---|---|---|---|---|
| 29 | 3-OCH$_3$-phenyl | S | (CH$_2$)$_2$ | s | 2 | Free base: Yield: 63.5%, oil Oxalate: m.p. 154.5–156.5° C. (decomp., recrystallized from acetone) |
| 30 | phenyl | S | (CH$_2$)$_2$ | s | 4 | Free base: Yield: 55.4%, m.p. 135–137° C. (recrystallized from ethanol) Oxalate: m.p. 98–105° C.(decomp., washed with ether) |
| 31 | phenyl | S | (CH$_2$)$_2$ | d | 4 | Free base: oil Oxalate.½H$_2$O: m.p. 116–120° C. (decomp., recrystallized from acetone) |

TABLE 7-continued

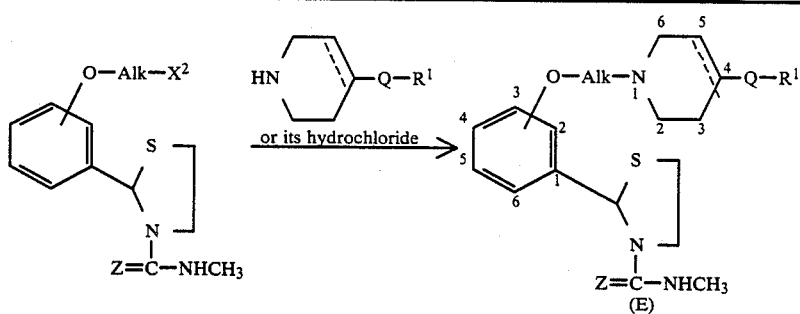

| Example Nos. | Q—R¹ | Z | Alk | 4-5* Bond | position** | Properties |
|---|---|---|---|---|---|---|
| 32 | (phenyl) | S | (CH₂)₃ | d | 4 | Free base: Yield: 53.8%, m.p. 137–139° C. (recrystallized from ethyl acetate n-hexane) Fumarate: m.p. 167–169° C. (decomp., recrystallized from methanol-acetone-ether) |
| 33 | (phenyl) | S | (CH₂)₃ | s | 4 | Free base: Yield: 59.8%, m.p. 132–134° C. (recrystallized from ethyl acetate-n-hexane) Fumarate: m.p. 176–177.5° C. (recrystallized from ether) |
| 34 | (phenyl) | O | (CH₂)₂ | s | 2 | Free base: Yield: 84%, m.p. 204–205° C. (washed with ether) Oxalate: m.p. 168–169° C. (decomp.) |
| 35 | (phenyl) | O | (CH₂)₂ | d | 2 | Free base: Yield: 61%, m.p. 143–145° C. (recrystallized from ethanol) Oxalate: m.p. 183–184° C. (decomp.) |
| 36 | (3-F-phenyl) | O | (CH₂)₂ | s | 2 | Free base: Yield: 78%, m.p. 195–198° C. (recrystallized from ethanol) Oxalate: m.p. 168–170° C. (decomp.) |
| 37 | (3-F-phenyl) | O | (CH₂)₂ | d | 2 | Free base: Yield: 58%, m.p. 166–168° C. (recrystallized from ethanol) Oxalate: m.p. 179–181° C. (decomp.) |
| 38 | (3-CH₃-phenyl) | O | (CH₂)₂ | s | 2 | Free base: Yield: 72%, m.p. 167–168° C. (recrystallized from ethanol) Oxalate: m.p. 163–164° C. (decomp.) |
| 39 | (3-CH₃-phenyl) | O | (CH₂)₂ | d | 2 | Free base: Oil Oxalate: m.p. 175–176° C. (decomp.) |

TABLE 7-continued

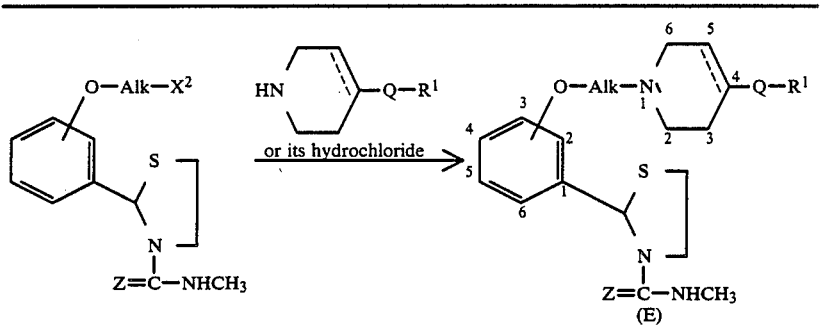

|  | Compound (E) | | | | |
|---|---|---|---|---|---|
| Example Nos. | Q—R¹ | Z | Alk | 4-5* Bond | position** | Properties |
| 40 | (3-methylphenyl) | O | $(CH_2)_2$ | s | 2 | Free base: Yield: 85.2% m.p. 130–132.5° C. (washed with ether) Oxalate: m.p. 142.5–144.5° C. (decomp., recrystallized from acetone) |
| 41 | (3-methoxyphenyl) | O | $(CH_2)_2$ | d | 2 | Free base: Yield: 58%, m.p. 125–127° C. (recrystallized from ethyl acetate-ether) Oxalate: m.p. 177–178° C. (decomp., recrystallized from ethanol-ether) |
| 42 | (phenyl) | O | $(CH_2)_3$ | d | 2 | Free base: Yield: 64%, m.p. 90–93° C. (washed with ether) Oxalate: m.p. 112–115° C. (recrystallized from ethanol-ether) |
| 43 | (3-fluorophenyl) | O | $(CH_2)_3$ | s | 2 | Free base: m.p. 124–127° C. (recrystallized from ethyl acetate-n-hexane) Fumarate: m.p. 135–146° C. (decomp., recrystallized from acetone) |
| 44 | $-CH_2-$(phenyl) | O | $(CH_2)_3$ | s | 2 | Free base: Yield: 53.7%, m.p. 130–132° C. (recrystallized from ethyl acetate-n-hexane) Oxalate: m.p. 95–105° C. (decomp., recrystallized from acetone-n-hexane) |
| 45 | (phenyl) | O | $(CH_2)_3$ | s | 4 | Free base: Yield: 70.6%, m.p. 129–131° C. (recrystallized from ethyl acetate-acetone-n-hexane Oxalate: m.p. 73–80° C. (decomp., recrystallized from acetone-methanol-n-hexane) |
| 46 | (phenyl) | O | $(CH_2)_3$ | d | 4 | Free base: Yield: 51%, m.p. 115–116° C. (recrystallized from ethyl acetate-ether) Oxalate: m.p. 115–116° C. (decomp., recrystallized from ethanol) |

TABLE 7-continued

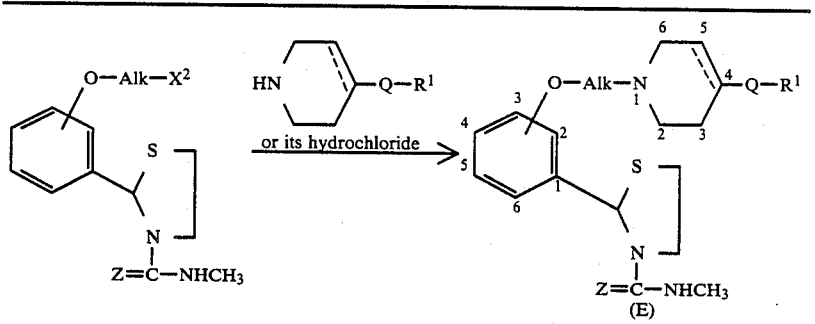

| Example Nos. | Compound (E) | | | | | Properties |
|---|---|---|---|---|---|---|
| | Q—R¹ | Z | Alk | 4-5* Bond | position** | |
| 47 | phenyl | O | (CH₂)₂ | d | 4 | Free base:<br>Yield: 84%, oil<br>IR $\nu_{max}^{liq}$ (cm$^{-1}$): 3400, 3300, 1620, 1000<br>Mass(m/e): 423, 366, 322, 184, 172<br>Oxalate.½EtOH:<br>m.p. 120–121° C. (decomp., recrystallized from ethanol) |
| 48 | phenyl | O | (CH₂)₂ | s | 4 | Free base:<br>Yield: quantitative, oil<br>IR $\nu_{max}^{liq}$ (cm$^{-1}$): 3400, 3330, 1630, 1610<br>Oxalate:<br>colorless caramel |
| 49 | phenyl | O | (CH₂)₃ | s | 2 | Free base:<br>Yield: 67.2%, m.p. 113–115.5° C. (recrystallized from ethyl acetate-isopropyl ether)<br>Oxalate.½H₂O:<br>m.p. 113–117° C. (decomp., recrystallized from ethanol-acetone-ether) |
| 50 | 3-methylphenyl | S | (CH₂)₃ | d | 2 | Free base:<br>m.p. 109–112° C. (recrystallized from ethyl acetate-n-hexane)<br>Oxalate:<br>m.p. 162–165.5° C. (decomp., recrystallized from ethanol-acetone-ether) |
| 51 | —CH₂-phenyl | S | (CH₂)₃ | d | 2 | Free base:<br>oil<br>IR $\nu_{max}^{liq}$ (cm$^{-1}$): 3320, 1680, 1595,<br>Oxalate:<br>m.p. 156–159° C. (decomp., recrystallized from acetone) |
| 52 | 3-fluorophenyl | O | (CH₂)₃ | d | 2 | Free base:<br>m.p. 70–73° C. (recrystallized from ethyl acetate-n-hexane)<br>Oxalate.½H₂O:<br>m.p. 139–142° C. (decomp.) |

Note:
Example Nos. 29–46 and 49–52: X² = Cl
Example Nos. 47–48: X² = Br
*The same as defined in the footnote of Table 1.
**Position means the position of the group:

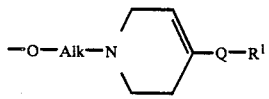

which is substituted on the benzene ring (the carbon atom of benzene ring which carries a thiazolidine group is taken as the 1-position).

EXAMPLE 53

A mixture of 1.5 g of 2-[2-(4-phenylpiperidin-1-yl)ethyloxy]benzaldehyde, 0.61 g of cycsteamine hydrochloride, 0.22 g of sodium hydroxide and 30 ml of ethanol is refluxed for one hour. 0.57 g of methyl isothiocyanate is added to the mixture, and the mixture is refluxed for 1.5 hours. The mixture is evaporated to remove the solvent. Water is added to the residue, and the aqueous solution is extracted with ethyl acetate. The extract is washed with water, dried and then evaporated to remove the solvent. The residue is recrystallized from a mixture of water and ethanol. 1.91 g of N-methyl-2-{2-[2-(4-phenylpiperidin-1-yl)ethyloxy]phenyl}thiazolidine-3-carbothioamide are obtained. Yield: 89.3%.

m.p. 141°–142° C.

Oxalate: m.p. 178°–180° C. (decomp., recrystallized from a mixture of methanol and ether.)

EXAMPLES 54 to 70

The following compounds (F) and (G) are obtained from the corresponding starting compounds in the same manner as described in Example 53.

TABLE 8

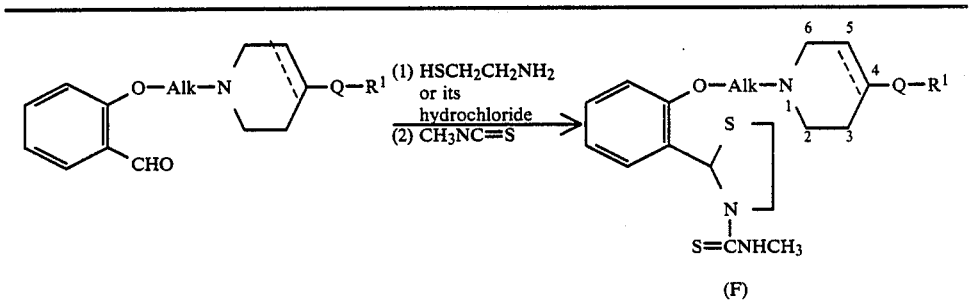

(F)

| Example Nos. | Q—R¹ | Alk | 4–5* Bond | Properties |
|---|---|---|---|---|
| 54 | —CH₂—⌬ | (CH₂)₃ | s | Free base: Yield: 65%, m.p. 90–92° C. Oxalate: m.p. 141–145° C. (decomp., recrystallized from ethanol-ether-isopropanol) |
| 55 | —⌬ | (CH₂)₃ | d | Free base: m.p. 141–144° C. (recrystallized from ethanol) Hydrochloride.½H₂O: m.p. 207–210.5° C. (decomp., recrystallized from ethanol-methanol-ether) |
| 56 | —⌬ | (CH₂)₃ | s | Free base: Yield: 51%, m.p. 120–126° C. (recrystallized from ethyl acetate-n-hexane) Hydrochloride.H₂O: m.p. 109–129° C. (decomp., recrystallized from isopropanol-isopropyl ether) |
| 57 | —⌬ | (CH₂)₂ | d | Free base: m.p. 140–146° C. Hydrochloride: m.p. 208–212.5° C. (decomp., recrystallized from methanol-ethanol-ether) |
| 58 | —⌬-F | (CH₂)₂ | s | Free base: Yield: 71.9%, m.p. 142–142.5° C. (recrystallized from ethyl acetate-n-hexane) Fumarate: m.p. 133–139° C. (decomp., recrystallized from methanol-ether) |
| 59 | —⌬-F | (CH₂)₂ | s | Free base: Yield: 59.5%, m.p. 147–148.5° C. (recrystallized from ethyl acetate-n-hexane) Oxalate: m.p. 155–159° C. (decomp., recrystallized from methanol-ether) |
| 60 | —⌬—OCH₃ | (CH₂)₃ | d | Free base: Yield: 89.8%, m.p. 169–171° C. (recrystallized from ethyl acetate-n-hexane) Oxalate: m.p. 188–190° C. (decomp., recrystallized from aqueous methanol) |

TABLE 8-continued

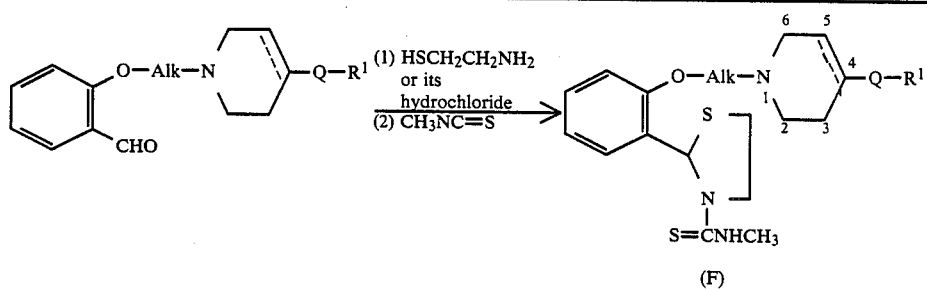

(F)

| Example Nos. | Compound (F) Q—R¹ | Alk | 4-5* Bond | Properties |
|---|---|---|---|---|
| 61 | —⟨benzene⟩—OCH₃ (para) | (CH₂)₂ | d | Free base: Yield: 88.1%, m.p. 150–153° C. (recrystallized from ethanol ether) Oxalate: m.p. 144–146° C. (decomp., recrystallized from methanol-ether) |
| 62 | —⟨benzene⟩—OCH₃ (para) | (CH₂)₂ | s | Free base: Yield: 76.7%, m.p. 146° C. (recrystallized from ethanol-ether-n-hexane) Oxalate: m.p. 185–187° C. (decomp., recrystallized from methanol-ether) |
| 63 | —⟨benzene⟩—OCH₃ (para) | (CH₂)₃ | s | Free base: Yield: 85%, m.p. 131–132.5° C. (recrystallized from ethanol-ether) Oxalate: m.p. 188.5–189.5° C. (decomp., recrystallized from methanol-ether) |
| 64 | —⟨benzene⟩—F (meta) | (CH₂)₃ | d | Free base: Yield: 54.8%, m.p. 125.5–127° C. (recrystallized from ethyl acetate-n-hexane) Oxalate: m.p. 201–202° C. (decomp., recrystallized from acetone) |
| 65 | —⟨benzene⟩—F (meta) | (CH₂)₃ | s | Free base: Yield: 90%, m.p. 151–152.5° C. (recrystallized from ethyl acetate-n-hexane) Oxalate: m.p. 189–191° C. (decomp., recrystallized from acetone) |
| 66 | —CH₂—⟨benzene⟩ | (CH₂)₂ | s | Free base: Yield: 66.5%, m.p. 113–114.5° C. (recrystallized from ethyl acetate-n-hexane) Fumarate: m.p. 168–178° C. (decomp., recrystallized from acetone) |
| 67 | —⟨benzene⟩—CH₃ (meta) | (CH₂)₂ | d | Free base: Yield: 78.8%, m.p. 122.5–125.5° C. (washed with ether) Oxalate.H₂O: m.p. 156–158° C. (decomp., recrystallized from acetone) |
| 68 | —⟨benzene⟩—CH₃ (meta) | (CH₂)₂ | s | Free base: Yield: 79.3%, m.p. 135.5–138.5° C. (washed with ether) Oxalate.H₂O: m.p. 152–154° C. (decomp., recrystallized from acetone) |

Note;
*The same as defined in the footnote of TABLE 1.

TABLE 9

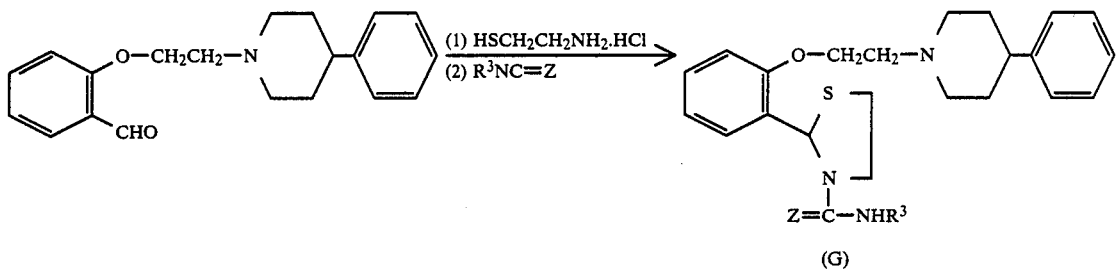

(G)

| Example Nos. | Compound (G) R³ | Z | Properties |
|---|---|---|---|
| 69 | CH₂CH₃ | S | Free base: m.p. 72–77.5° C. |
| | | | Fumarate.½H₂O: m.p. 153–157.5° C. (decomp., recrystallized from acetone) |
| 70 | CH₂CH₂CH₂CH₃ | O | Free base: |
| | | | Yield: 68.7%, m.p. 130–133° C. (recrystallized from ethyl acetate-n-hexane) |
| | | | Oxalate: |
| | | | m.p. 170–174° C. (decomp., recrystallized from acetone) |

EXAMPLE 71

676 mg of sodium isocyanate, 20 ml of water and 1.56 g of acetic acid are added to a solution of 2 g of 2-{2-[2-(4-(3-fluorophenyl)-1,2,3,6-tetrahydropyridin-1-yl)ethyloxy]phenyl}thiazolidine in 40 ml of ethanol, and the mixture is stirred at room temperature for 4 hours. Th mixture is poured into water. The aqueous solution is alkalized with potassium carbonate, and then extracted with ethyl acetate. The extract is washed with water, dried and then evaporated to remove the solvent. The residue is purified by silica gel column chromatography (solvent, ethyl acetate:methanol=20:1), whereby 1.59 g of 2-{2-[2-(4-(3-fluorophenyl)-1,2,3,6-tetrahydropyridin-1-yl)ethyloxy]phenyl}thiazolidine-3-carboxamide are obtained as pale yellow crystals.

Yield: 71.6%.

m.p. 148°–151° C. (recrystallized from ethyl acetate).

Oxalate:

m.p. 168°–170° C. (decomp., recrystallized from acetone).

EXAMPLE 72

1.33 g of potassium carbonate are added to 20 ml of dimethylformamide containing 2.31 g of 2-{2-[2-(4-(3-fluorophenyl)-1,2,3,6-tetrahydropyridin-1-yl)ethyloxy]phenyl}thiazolidine, and a solution of 968 mg of N,N-dimethylcarbamoyl chloride in 10 ml of dimethylformamide is added dropwise thereto. The mixture is stirred at 50° C. for 5 hours. The mixture is poured into water, and the aqueous solution is extracted with ethyl acetate. The extract is washed with water, dried and then evaporated to remove the solvent. The residue is purified by silica gel column chromatography (solvent, benzene:ethyl acetate=1:1), whereby 1.26 g of N,N-diemthyl-2-{2-[2-(4-(3-fluorophenyl)-1,2,3,6-tetrahydropyridin-1-yl)ethyloxy]phenyl}thiazolidine-3-carboxamide are obtained as colorless caramel.

IR$\nu_{max}^{CHCl_3}$ (Cm⁻¹): 1640

Oxalate:

m.p. 154.5°–158.5° C. (decomp., recrystallized from acetone).

EXAMPLE 73

2.31 g of 2-{2-[2-(4-(3-fluorophenyl)-1,2,3,6-tetrahydropyridin-1-yl)ethyloxy]phenyl}thiazolidine are dissolved in 15 ml of acetone, and 0.61 g of acetyl isocyanate is added thereto. The mixture is stirred at room temperature for 30 minutes, and then 0.17 g of acetyl isocyanate is added to the mixture. The mixture is further stirred at room temperature for 20 hours. The mixture is evaporated under reduced pressure to remove the solvent. Water is added to the residue, and the aqueous solution is extracted with ethyl acetate. The extract is washed with a saturated sodium chloride solution, dried and then evaporated to remove the solvent. The residue is purified by silica gel column chromatography (solvent. chloroform:methanol=20:1), whereby 1.9 g of N-acetyl-2-{2-[2-(4-(3-fluorophenyl)-1,2,3,6-tetrahydropyridin-1-yl)ethyloxy]phenyl}thiazolidine-3-carboxamide are obtained.

m.p. 119°–121° C. (recrystallized from a mixture of ethyl acetate and ether).

Oxalate.½H₂O:

m.p. 130°–132° C. (decomp., recrystallized from a mixture of acetone and ether).

EXAMPLE 74

A mixture of 2.69 g of 2-{2-[2-(4-(3-fluorophenyl)-1,2,3,6-tetrahydropyridin-1-yl)ethyloxy]phenyl} thiazolidine, 0.78 g of acetyl isothiocyanate and 20 ml of acetone is stirred at room temperature for 2 hours. The reaction mixture is treated in the same manner as described in Example 73. 2.2 g of N-acetyl-2-{2-[2-(4-(3-fluorophenyl)-1,2,3,6-tetrahydropyridin-1-yl)ethyloxy]phenyl}thiazolidine-3-carbothioamide are obtained. Yield: 65%.

m.p. 135°–136° C. (recrystallized from mixture of chloroform and ether).

Oxalate:

m.p. 165°–166° C. (decomp., recrystallized from a mixture of acetone and ether).

EXAMPLE 75

A mixture of 1.47 g of N-methyl-2-{2-[2-(4-phenyl-piperidin-1-yl)ethyloxy]phenyl}thiazolidine-3-carbothioamide, 0.70 g of methyl trans-3-(4-methoxyphenyl)-glycidate and 30 ml of ethanol is refluxed for 7 hours.

0.70 g of methyl trans-3-(4-methoxyphenyl)glycidate is added to the mixture, and the mixture is further refluxed for 5 hours. The mixture is evaporated to remove the solvent. The residue is purified by silica gel column chromatography (solvent, chloroform:ethanol=30:1), whereby 1.17 g of N-methyl-2-{2-[2-(4-phenylpiperidine-1-yl)ethyloxy]phenyl}thiazolidine-3-carboxamide are obtained. Yield: 82.3%.

m.p. 204°–205° C. (washed with ethanol).
Oxalate:
m.p. 168°–169° C. (decomp.).

EXAMPLES 76 to 79

The following compounds are obtained from the corresponding starting compounds in the same manner as described in Example 75.

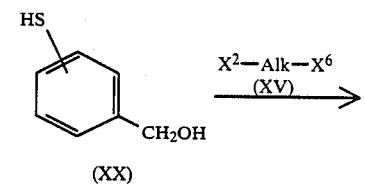

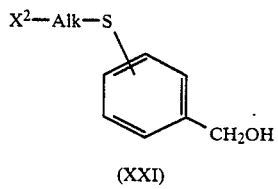

TABLE 10

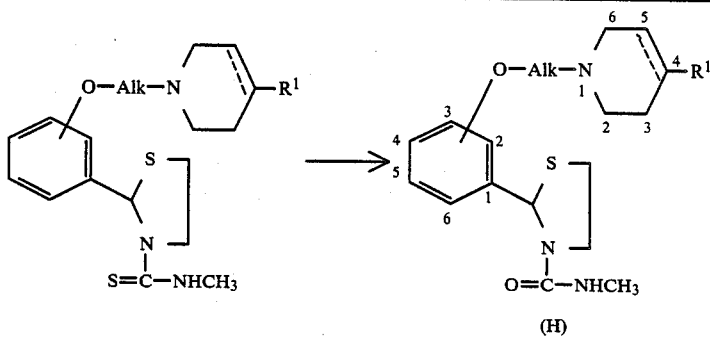

(H)

| Example Nos. | R¹ | Alk | 4-5* Bond | Position** | Properties |
|---|---|---|---|---|---|
| 76 | 3-methylphenyl (CH₃) | $(CH_2)_2$ | s | 2 | Free base: Yield: 85.4%, m.p. 167–168° C. (recrystallized from ethanol) Oxalate: m.p. 163–164° C. (decomp.) |
| 77 | 3-methoxyphenyl (OCH₃) | $(CH_2)_2$ | d | 2 | Free base: Yield: 65.6%, m.p. 125–127° C. (recrystallized from ethyl acetate-ether) Oxalate: m.p. 177–178° C. (decomp., recrystallized from ethanol-ether) |
| 78 | 3-fluorophenyl (F) | $(CH_2)_2$ | d | 2 | Free base: Yield: 58.7%, m.p. 166–168° C. (recrystallized from ethanol) Oxalate: m.p. 179–181° C. (decomp.) |
| 79 | phenyl | $(CH_2)_3$ | d | 4 | Free base: Yield: 82.0%, m.p. 115–116° C. (recrystallized from ethyl acetate-ether) Oxalate: m.p. 115–116° C. (decomp., recrystallized from ethanol) |

Note;
*, **The same as defined in the footnote of Table 1.

Preparation of Starting Compounds

Preparation 1 wherein Alk, $X^2$ and $X^6$ are the same as defined above.

This reaction may be readily conducted at 0° to 100° C. in the presence of an acid acceptor such as those described in Processes (A) to (D).

The practical embodiments of the above-mentioned reaction are as follows:

A mixture of 11.9 g of 2-(hydroxymethyl)thiophenol, 35.44 g of 1-bromo-3-chloropropane, 11.58 g of potassium carbonate and 150 ml of dimethylformamide is stirred at room temperature for 2 hours. Insoluble materials are filtered off, and the filtrate is concentrated under reduced pressure to remove solvent. Water is added to the residue, and the aqueous mixture is extracted with ethyl acetate. The extract is washed with water, dried and concentrated under reduced pressure to remove solvent. The residue is distilled under reduced pressure. 16.8 g of 2-(3-chloropropylthio)benzylalcohol are obtained as colorless oil. Yield: 93%.

B.p. 148°–159° C. (0.25 mmHg).

IR $\nu_{max}^{liq}$ (cm$^{-1}$): 3350, 1580, 1430, 1030, 750

The following compound is obtained from the corresponding starting compounds in the same manner as described above.

TABLE 11

| Compound (XXI) | | | |
|---|---|---|---|
| $X^2$ | Alk | position* | Properties |
| Cl | —(CH$_2$)$_2$— | 2 | Yield: 75.5% B.p. 143–148° C. (0.6 mmHg) |

Note:
$X^6$ = Br
*Position means the position of the $X^2$—Alk—S— group which is substituted on the benzene ring (the carbon atom of benzene ring which carries a hydroxymethyl group is taken as the 1-position.

Preparation 2

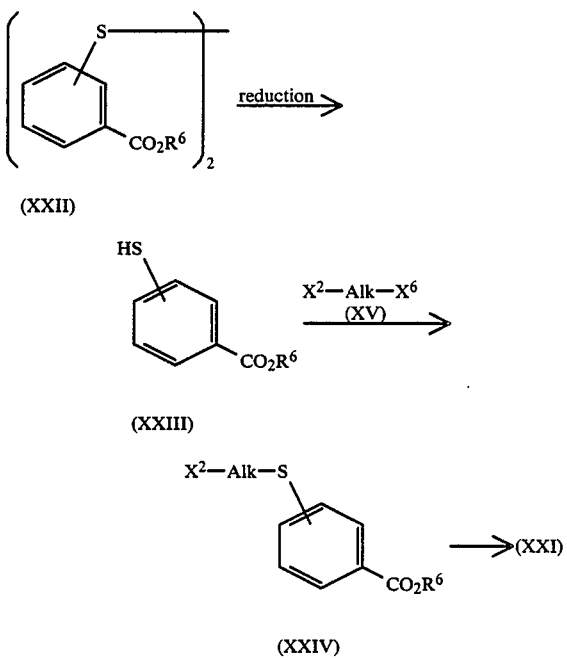

wherein $R^6$ is a lower alkyl group and Alk, $X^2$ and $X^6$ are the same as defined above.

The compound (XXIII) may be obtained by reducing the compound (XXII) with a reducing agent such as sodium borohydride or zinc and acetic acid at 0° to 100° C., and the subsequent reaction of the compounds (XXIII) and (XV) may be conducted in the same manner as described in Preparation 1. Reduction of the compound (XXIV) with a reducing agent such as lithium aluminum hydride or lithium borohydride at 0° to 30° C. gives the compound (XXI).

The practical embodiments of the above-mentioned reactions are as follows:

(i) 33.4 g of bis(4-methoxycarbonylphenyl)disulfide are suspended in a mixture of 200 ml of dioxane and 120 ml of methanol, and 5.7 g of sodium borohydride are added thereto under ice-cooling and stirring. 6 g of sodium hydride (60% oil dispersion) are added to the mixture, and a solution of 37.8 g of 1-bromo-3-chloropropane in 120 ml of dioxane is added thereto. The mixture is stirred at room temperature for one hour and further refluxed for one hour. 4 g of sodium borohydride, 4 g of sodium hydride (50% oil dispersion) and 8 g of 1-bromo-3-chloropropane are added to the mixture, and the mixture is refluxed for 30 minutes. The mixture is poured into ice-water, and the aqueous mixture is extracted with chloroform. The extract is washed with water, dried and concentrated under reduced pressure to remove solvent. The residue is distilled under reduced pressure. 31.9 g of methyl 4-(3-chloropropylthio)benzoate are obtained as pale yellow oil. Yield: 65%.

B.p. 155°–164° C. (0.3 mmHg).

5 g of lithium aluminum hydride are suspended in 200 ml of tetrahydrofuran, and a solution of 31.9 g of methyl 4-(3-chloropropylthio)benzoate in 200 ml of tetrahydrofuran is added thereto at 5° to 15° C. The mixture is stirred at the same temperature for 45 minutes. Water is added to the mixture at a temperature of below 20° C., and insoluble materials are filtered off. The filtrate is concentrated under reduced pressure to remove solvent, and the residue is distilled under reduced pressure. 24.1 g of 4-(3-chloropropylthio)benzylalcohol are obtained as an oil. Yield: 85%.

B.p. 144°–154° C. (0.35 mmHg).

(ii) 40.1 g of bis(4-methoxycarbonylphenyl)disulfide, 38 g of 1-bromo-2-chloroethane, 13 g of sodium borohydride, 13.6 g of sodium hydride (60% oil dispersion), 100 ml of methanol and 320 ml of dioxane are treated in the same manner as described in paragraph (i), whereby 36 g of methyl 4-(2-chloroethylthio)benzoate are obtained as a crude product. The crude product (36 g) is treated with 4.63 g of lithium aluminum hydride, whereby 16.3 g of 4-(2-chloroethylthio)benzylalcohol are obtained as a crude product. A mixture of the crude product (16.3 g) thus obtained, one ml of 10% hydrochloric acid and 100 ml of ethanol is stirred at 50° C. for 1.5 hours. The mixture is concentrated under reduced pressure to remove solvent. Water is added to the residue, and the aqueous mixture is extracted with ethyl acetate. The extract is washed with an aqueous sodium bicarbonate solution and water, dried and then concentrated under reduced pressure to remove solvent. The residue is purified by silica gel chromatography (solvent, chloroform). 10 g of 4-(2-chloroethylthio)benzylalcohol are obtained as an oil.

Mass (m/e): 202, 204, 153, 123, 107.

Preparation 3

$$X^2-Alk-S-\underset{CH_2OH}{\text{[benzene ring]}} \xrightarrow{\text{oxidation}}$$

(XXI)

$$X^2-Alk-S-\underset{CHO}{\text{[benzene ring]}}$$

(XXV)

wherein Alk and $X^2$ are the same as defined above.

The oxidation may be carried out by treating the compound (XXI) with dimethylsulfoxide and oxalyl chloride in the presence of a tertiary amine at $-60°$ to $30°$ C. or by treating the compound with manganese dioxide.

The practical embodiments of the above-mentioned reaction are as follows:

A solution of 27.8 g of dimethylsulfoxide in 50 ml of methylene chloride is added to a solution of 22.6 g of oxalyl chloride in 450 ml of methylene chloride at $-60°$ C. during one hour, and a solution of 32.7 g of 2-(2-chloroethylthio)benzylalcohol in 50 ml of methylene chloride is added thereto. The mixture is stirred for 15 minutes, and a solution of 71.8 g of triethylamine in 50 ml of methylene chloride is added to the mixture at $-60°$ C. The mixture is stirred at the same temperature for 5 minutes and further stirred at room temperature for one hour. Water is added to the mixture, and the methylene chloride layer is collected therefrom. The methylene chloride solution is washed with water, dried and concentrated under reduced pressure to remove solvent. The residue is distilled under reduced pressure. 29.7 g of 2-(2-chloroethylthio)benzaldehyde are obtained as an oil. Yield: 91.6%.

B.p. 135°-140° C. (0.4 mmHg).

$IR\nu_{max}^{(cm^{-1})}$: 1690

The following compounds are obtained from the corresponding starting compounds in the same manner as described above.

TABLE 12

Compound (XXV)

| $X^2$ | Alk | position* | Properties |
|---|---|---|---|
| Cl | —(CH$_2$)$_3$— | 2 | Yield: 93.7% |
|  |  |  | B.p. 149-151° C. (0.7 mmHg) |
|  |  |  | $IR\nu_{max}^{liq}$ (cm$^{-1}$): 1690 |
| Cl | " | 4 | Yield: 92% oil |
|  |  |  | $IR\nu_{max}^{liq}$ (cm$^{-1}$): 1680, 1660 |
| Cl | —(CH$_2$)$_2$— | " | Yield: 93% oil |

Note:
*Position means the position of the $X^2$—Alk—S— group which is substituted on the benzene ring (the carbon atom of benzene ring which carries a formyl group is taken as the 1-position).

Preparation 4

$$HO-\underset{CHO}{\text{[benzene ring]}} + X^2-Alk-X^6 \longrightarrow$$

(XXVI)   (XV)

$$X^2-Alk-O-\underset{CHO}{\text{[benzene ring]}}$$

(XXVII)

wherein Alk, $X^2$ and $X^6$ are the same as defined above.

The reaction of the compound (XXVI) with (XV) may be carried out in the same manner as described in Preparation 1.

Tht practical embodiments of the above-mentioned reactions are as follows:

40.0 g of 2- hydroxybenzaldehyde, 84 g of 1-chloro-2-tosyloxyethane and 50 g of potassium carbonate are added to 270 ml of dimethylformamide, and the mixture is stirred at room temperature for 3 days. After the reaction, half of the solvent is distilled off under reduced pressure. About 600 ml of water are added to the residue, and the mixture is extracted with ether. The extract is washed with 10% sodium hydroxide solution and water, dried and then distilled to remove the solvent. The residue is distilled at 116°-118° C./0.2-0.3 mmHg to give 2-(2-chloroethyloxy)benzaldehyde (51.9 g, yield: 86%) as a coloress oil. The properties of this compound are the same as those disclosed in J.O.C., 18, 1380-1402 (1953).

The compounds shown in Table 13 are obtained from the corresponding starting compounds in the same manner as described above.

TABLE 13

Compound (XXVII)

| $X^2$ | Alk | Position* | Properties |
|---|---|---|---|
| Cl | —(CH$_2$)$_3$— | 2 | Yield: 85%,*2 |
|  |  |  | The physical properties are the same as those disclosed in Japanese Patent Publication No. 21126/1974 |
| Cl | —(CH$_2$)$_2$— | 4 | Yield: 59.5% |
|  |  |  | b.p. 116-118° C./0.25 mmHg*3 |
| Cl | —(CH$_2$)$_3$— | 4 | Yield: 76.6% |
|  |  |  | b.p. 130-135° C./0.35 mmHg |
|  |  |  | $IR\nu_{max}^{liquid}$ (cm$^{-1}$): 1680*2 |

*Position means the position of the $X^2$—Alk—O—group which is substituted on the benzene ring (the carbon atom of benzene ring which carries a formyl group is taken as the 1-position)
*2 The compound of the formula: $X^2$—Alk—$X^6$ ($X^2$ = Cl, $X^6$ = Br) is used as the starting compound.
*3 The compound of the formula: $X^2$—Alk—$X^6$ ($X^2$ = Cl, $X^6$ = tosyloxy) is used as the starting compound.

Preparation 5

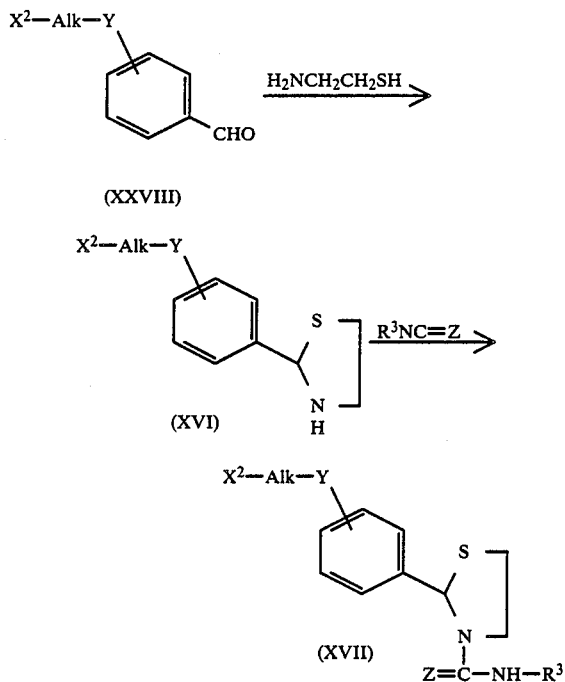

wherein $R^3$, Alk, Y, Z and $X^2$ are the same as defined above.

The reaction of the compound (XXVIII) and cysteamine or its salt may be conducted in the same manner as in the case of the reaction of the compound (XVIII) and cysteamine, and the product (XVI) thus obtained may be used without purification/isolation for the subsequent step to produce the compound (XVII).

The practical embodiments of the above-mentioned reactions are as follows:

3.34 g of sodium hydroxide and 9.21 g of cysteamine hydrochloride are added to a solution of 14.8 g of 2-(2-chloroethylthio)benzaldehyde in 300 ml of ethanol, and the mixture is stirred at room temperature for 16 hours. The mixture is concentrated under reduced pressure to remove solvent, and 300 ml of tetrahydrofuran and 5.04 g of methyl isocyanate are added to the residue. The mixture is stirred at room temperature for 20 hours and then concentrated under reduced pressure to remove solvent. Water is added to the residue, and the aqueous mixture is extracted with chloroform. The extract is washed with water, dried and concentrated under reduced pressure to remove solvent. The residue it purified by silica gel chromatography (solvent, chloroform-:ethanol=50:1). 11.3 g of N-methyl-2-[2-(2-chloroethylthio)phenyl]thiazolidine-3-carboxamide are obtained.

M.p. 123°–125° C.

The following compounds are obtained from the corresponding starting compounds in the same manner as described above.

TABLE 14

| Compound (XVII) | | | | | | |
|---|---|---|---|---|---|---|
| $X^2$ | Alk | Position* | $R^3$ | Z | Y | Properties |
| Cl | —(CH$_2$)$_3$— | 2 | CH$_3$ | O | S | Yield: 76.3% M.p. 116–118° C. (recrystallized from ethanol-ether) |
| Cl | —(CH$_2$)$_3$— | " | " | S | " | Yield: 73.6% M.p. 140–142° C. |
| Cl | —(CH$_2$)$_2$— | " | " | " | " | (recrystallized from ethanol) M.p. 134–136° C. |
| Cl | " | 4 | " | " | " | Yield: 51% oil Mass (m/e): 332, 334, 258, 198 |
| Cl | " | " | " | O | " | Yield: 72% oil Mass (m/e): 316, 318, 257, 198 |
| Cl | —(CH$_2$)$_3$— | " | " | " | " | M.p. 102–105° C. |
| Cl | " | " | " | S | " | Yield: 60% M.p. 120.5–122.5° C. |
| Cl | —(CH$_2$)$_2$— | 2 | " | O | O | Yield: 70% M.p. 166–167° C. (recrystallized from ethanol-ether) |
| Cl | —(CH$_2$)$_3$— | " | " | " | " | Yield: 63% M.p. 128–130° C. (recrystallized from methanol-ether) |
| Br | —(CH$_2$)$_2$— | 4 | " | " | " | Yield: 71.9% M.p. 96–98.5° C. (recrystallized from ethyl acetate-ether-n-hexane) |
| Cl | —(CH$_2$)$_3$— | " | " | " | " | Yield: 87.2% M.p. 75–78° C. (recrystallized from etyl acetate-ether n-hexane) |
| Cl | —(CH$_2$)$_2$— | 2 | " | S | " | Yield: 71% M.p. 153–154.5° C. (recrystallized from ethanol) |
| Cl | —(CH$_2$)$_3$— | " | " | " | " | Yield: 52.8% M.p. 118–120° C. (recrystallized from ethyl acetate-n-hexane) |
| Cl | —(CH$_2$)$_2$— | 4 | " | " | " | Yield: 50.3%; m.p. 114–116° C. (recrystallized from ethanol) |
| Cl | —(CH$_2$)$_3$— | " | " | " | " | Yield: 84.1%; m.p. 127.5–128.5° C. (recrystallized from ethanol) |

*Position means the position of the $X^2$—Alk—Y- group which is substituted on the benzene ring (the carbon atom of benzene ring which carries a thiazolidine group is taken as the 1-position).

Preparation 6

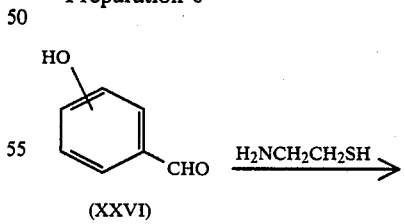

(XXVI)

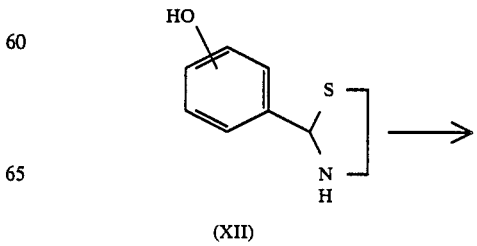

(XII)

-continued

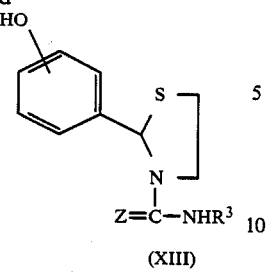

(XIII)

wherein R³ and Z are the same as defined above.

The reaction of the compound (XXVI) and cysteamine or its salt may be conducted in the same manner as in the case of the reaction of the compound (XVIII) and cysteamine. It is preferred to carry out the reaction in an inert gas atmosphere. The product (XII) obtained may be used without purification/isolation for the subsequent step to give the compound (XIII).

The practical embodiments of the above-mentioned reaction are as follows:

(1) To a solution of cysteamine hydrochloride (11.3 g) in ethanol (250 ml) is added sodium hydroxide (4.0 g), and the mixture is stirred for 30 minutes under argon gas. A solution of 2-hydroxybenzaldehyde (12.2 g) in ethanol (40 ml) is added to the mixture, and the mixture is refluxed for 4 hours. To the mixture is added methyl isothiocyanate (7.9 g), and the mixture is further refluxed for 4 hours. After distilling off the solvent under reduced pressure, a mixture of water and ethanol is added to the resulting residue, and the insoluble crystals are collected by filtration. The crystals thus obtained are washed with water and ethanol and recrystallized from ethanol to give N-methyl-2-(2-hydroxyphenyl)-thiazolidine-3-carbothioamide (7.9 g, yield: 31.1%).

M.p. 179°–182.5° C. (decomp.).

(2) A mixture of 5.65 g of cysteamine hydrochloride, 2 g of sodium hydroxide and 150 ml of ethanol is refluxed for 15 minutes. A solution of 6.1 g of 2-hydroxybenzaldehyde in 30 ml of ethanol is added to the mixture, and the mixture is refluxed for 2 hours. The mixture is concentrated under reduced pressure to remove solvent. Benzene is added to the residue, and the mixture is concentrated under reduced pressure to remove solvent. 120 ml of tetrahydrofuran are added to the residue, and the mixture is stirred at room temperature for 1.5 hours. 3.5 of methyl isocyanate are added to the mixture, and the mixture is stirred at room temperature for 30 minutes and further refluxed for one hour. The mixture is concentrated under reduced pressure to remove solvent. Water is added to the residue, and crystalline precipitates are collected by filtration. The crystals are washed with water and ethyl acetate, dried and then recrystallized from ethanol. 8.97 g of N-methyl-2-(2-hydroxyphenyl)thiazolidine-3-carboxamide are obtained. Yield: 75.4%.

M.p. 186°–188° C. (decomp.).

(3) 5.68 g of cysteamine hydrochloride, 2 g of sodium hydroxide, 6.1 g of 4-hydroxybenzaldehyde and 3.5 g of methyl isocyanate are treated in the same manner as described in paragraph 2. 8.1 g of N-methyl-2-(4-hydroxyphenyl)thiazolidine-3-carboxamide are obtained. Yield: 68.1%.

M.p. 218°–220° C. (recrystallized from ethanol).

Preparation 7

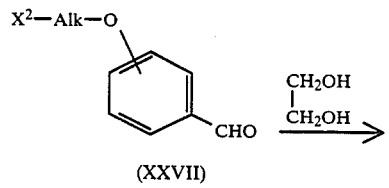

(XXVII)

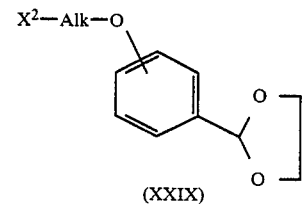

(XXIX)

wherein X² and Alk are the same as defined above.

The reaction of the compound (XXVII) and ethylene glycol may be conducted in a solvent (e.g., benzene, toluene or xylene) in the presence of an acid (e.g., phosphoric acid, hydrochloric acid, sulfuric acid, toluenesulfonic acid or acidic ion exchange resin) at 80° to 140° C.

The practical embodiments of the above-mentioned reaction are as follows:

To a solution of 46.5 g of 2-(2-chloroethyloxy)benzaldehyde obtained in Preparation 4 and 33.2 g of ethylene glycol in 500 ml of benzene is added 0.5 ml of 85% phosphoric acid, and the mixture is refluxed with stirring for about 18 hours while removing the produced water. After the reaction, the reaction mixture is cooled with ice and is made alkaline with saturated sodium bicarbonate solution to separate into two layers. The benzene layer is taken, washed with saturated saline solution, dried and then distilled to remove the solvent. The crude product thus obtained is distilled to give 56 g of 2-(2-chloroethyloxy)benzaldehyde ethyleneacetal (yield: 97%) as a colorless oil. b.p. 130°–135° C./0.3 mmHg.

IR$\nu_{max}^{liquid}$ (cm$^{-1}$): 1600, 1490, 760

NMR (CDCl₃) δ:

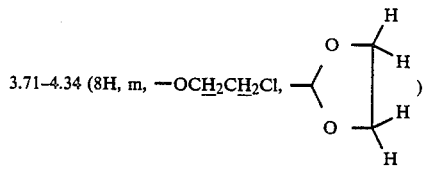

3.71–4.34 (8H, m, —OCH₂CH₂Cl,

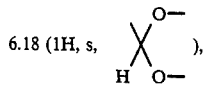

6.18 (1H, s,

Preparation 8

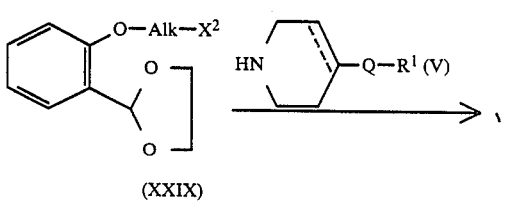

(XXIX)

-continued

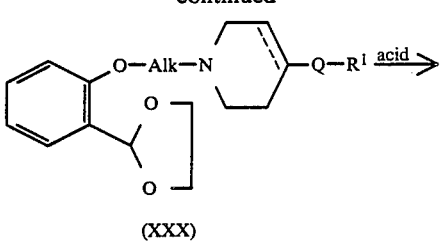

(XXX)

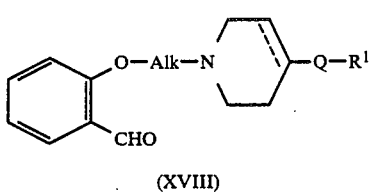

(XVIII)

wherein $R^1$, Q, Alk, $X^2$ and the group:

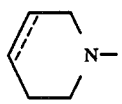

are the same as defined above.

The compound (XVIII) may be prepared, for example, by reacting the compound (XXIX) and (V) in the same manner as described in Process B to give the compound (XXX), and then treating it with an acid (e.g., hydrochloric acid, sulfuric acid or hydrobromic acid) at 0° to 100° C. in a solvent (e.g., alkanol, tetrahydrofuran, dioxane or a mixture of these solvents with water).

The practical embodiments of the above-mentioned reaction are as follows.

A mixture of 2.84 g of 2-(2-chloroethyloxy)benzaldehyde ethyleneacetal, 2.0 g of 4-phenylpiperidine, 1.89 g of potassium carbonate and 20 ml of dimethylformamide is stirred at 80° C. for 22 hours. The mixture is cooled and water is added thereto. The aqueous solution is extracted with ethyl acetate, dried and then evaporated to remove the solvent. The residue is purified by silica gel column chromatography (solvent, benzene:ethyl acetate=3:2), whereby 2.74 g of 2-[2-(4-phenylpiperidin-1-yl)ethyloxy]benzaldehyde ethyleneacetal are obtained as an oil.

The product thus obtained is dissolved in a solution of 20 ml of methanol and 20 ml of 10% HCl, and the mixture is stirred at 70° C. for 20 minutes. Water is added to the mixture. The mixture is alkalized with a 10% sodium hydroxide solution, and extracted with benzene. The extract is washed with water, dried and then evaporated to remove the solvent. The residue is recrystallized from a mixture of ether and n-hexane. 1.54 g of 2-[2-(4-phenylpiperidin-1-yl)ethyloxy]benzaldehyde are obtained.

M.p. 59°–62° C.

The following compounds are obtained from the corresponding starting compounds in the same manner as described above.

TABLE 15

| Compound (XVIII) | | | |
|---|---|---|---|
| $Q-R^1$ | Alk | 4–5* Bond | properties |
| phenyl | —(CH$_2$)$_3$— | s | Yield: 58%, oil $IR\nu_{max}^{liq}$ (cm$^{-1}$): 2930, 1680, 1590, 1240, 760 |
| —CH$_2$—phenyl | " | s | Yield: 94%, oil $IR\nu_{max}^{liq}$ (cm$^{-1}$): 1680, 1590 |
| phenyl | " | d | oil $IR\nu_{max}^{liq}$ (cm$^{-1}$): 1680, 1590 |
| phenyl | —(CH$_2$)$_2$— | d | oil $IR\nu_{max}^{liq}$: 1680, 1590 |
| 3-F-phenyl | " | s | Yield: 65.9%, oil $IR\nu_{max}^{liq}$ (cm$^{-1}$): 1680, 1590, 750 |
| 3-F-phenyl | " | d | Yield: 61.4%, oil $IR\nu_{max}^{liq}$ (cm$^{-1}$): 1680, 1590, 760 |

TABLE 15-continued

Compound (XVIII)

| Q—R$^1$ | Alk | 4-5* Bond | properties |
|---|---|---|---|
| 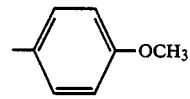 | " | d | m.p. 124–126° C. (recrystallized from ethyl acetate-n-hexane) |
| 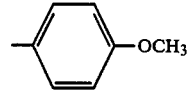 | —(CH$_2$)$_3$— | d | m.p. 90–93° C. (recrystallized from ethyl acetate-n-hexane) |
| 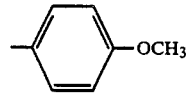 | —(CH$_2$)$_2$— | s | Yield: 59.1%, m.p. 79–82° C. (recrystallized from ethyl acetate-n-hexane) |
| 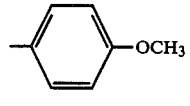 | —(CH$_2$)$_3$— | s | Yield: 71.9%, m.p. 52–56° C. (recrystallized from ethyl acetate-n-hexane) |
| 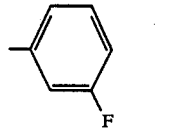 | " | d | Yield: 63.7%, oil IR$\nu_{max}^{liq}$ (cm$^{-1}$): 1680, 1590, 750 |
| 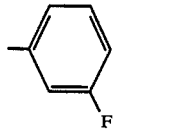 | " | s | Yield: 63.3%, oil IR$\nu_{max}^{liq}$ (cm$^{-1}$): 1680, 1590, 750 |
| 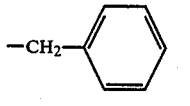 | —(CH$_2$)$_2$— | s | Yield: 82.9%, oil IR$\nu_{max}^{liq}$ (cm$^{-1}$): 1680, 1590, 750 |
| 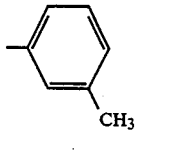 | " | s | oil IR$\nu_{max}^{liq}$ (cm$^{-1}$): 1680, 1590 |
| 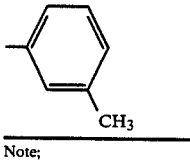 | " | d | oil IR$\nu_{max}^{liq}$ (cm$^{-1}$): 1680, 1590 |

Note;
*Same as defined in the footnote of Table 1.

Preparation 9

8.09 g of cysteamine hydrochlorideare dissolved in 450 ml of ethanol, and 2.93 g of sodium hydroxide are added thereto. The mixture is stirred at room temperature for 10 minutes. A solution of 21.05 g of 2-{2-[4-(3-fluorophenyl)-1,2,3,6-tetrahydropyridin-1-yl]ethyloxy}benzaldehyde in 50 ml of ethanol is added to the mixture, and the mixture is further stirred at room temperature for 14 hours. The mixture is concentrated and then extracted with ethyl acetate. The extract is washed with a saturated sodium chloride solution, dried and then evaporated to remove the solvent. The residue is recrystallized from n-hexane. 21.62 g of 2-{2-[2-(4-(3-fluorophenyl)-1,2,3,6-tetrahydropyridin-1-yl)ethyloxy]phenyl}thiazolidine are obtained. Yield: 69%.

m.p. 62°–65° C.

What we claim is:

1. A compound of the formula:

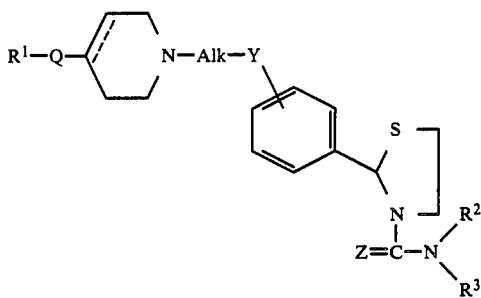 (I)

wherein R¹ is an unsubstituted phenyl group or a phenyl group substituted with a member selected from the group consisting of a halogen atom, a lower alkyl group, and a lower alkoxy group, R² is hydrogen or a lower alkyl group, R³ is hydrogen, a lower alkyl group or a lower alkanoyl group, Q is a single bond or a lower alkylene group, Alk is a lower alkylene group, Y and Z are the same or different and are an oxygen atom or a sulfur atom and the group of the formula:

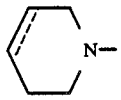

is either

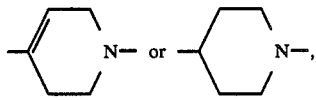

or a pharmaceutically acceptable salt thereof.

2. The compound claimed in claim 1, in which R¹ is phenyl which is unsubstituted or substituted with fluorine, methyl or methoxy, R² is hydrogen or methyl, R³ is hydrogen, methyl, ethyl, butyl or acetyl, Q is a single bond or methylene, and Alk is ethylene or trimethylene.

3. The compound claimed in claim 2, in which R¹ is phenyl, 3-fluorophenyl, 3-methylphenyl, 3-methoxyphenyl or 4-methoxyphenyl.

4. A compound of the formula:

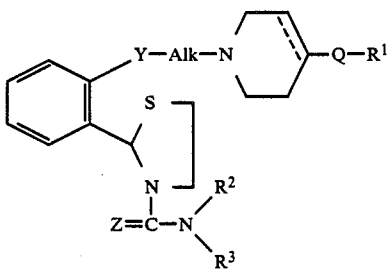 (I-A)

wherein R¹ is an unsubstituted phenyl group or a phenyl group substituted with a member selected from the group consisting of a halogen atom, a lower alkyl group, and a lower alkoxy group, R² is hydrogen or a lower alkyl group, R³ is hydrogen, a lower alkyl group or a lower alkanoyl group, Q is a single bond or a lower alkylene group, Alk is a lower alkylene group, Y and Z are the same or different and are an oxygen atom or a sulfur atom and the group of the formula:

is either

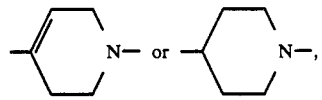

or a pharmaceutically acceptable salt thereof.

5. The compound in claim 4, in which R¹ is an unsubstituted phenyl or phenyl substituted with fluorine, methyl or methoxy, R² is hydrogen or methyl, R³ is hydrogen, methyl, ethyl, butyl, or acetyl, Q is a single bond or methylene, and Alk is ethylene or trimethylene.

6. The compound claimed in claim 5, in which R² is hydrogen, R³ is a lower alkyl group, Q is a single bond, Y is an oxygen atom and Z is an oxygen atom or a sulfur atom.

7. The compound claimed in claim 6, in which R¹ is phenyl, fluorophenyl, methylphenyl or methoxyphenyl, R³ is methyl, ethyl or butyl and Alk is ethylene or trimethylene.

8. The compound claimed in claim 7, in which R¹ is phenyl, 3-fluorophenyl, 3-methylphenyl, 3-methoxyphenyl or 4-methoxyphenyl, R³ is methyl and Alk is ethylene.

9. The compound according to claim 1, which is N-methyl-2-{2-[3-(4-phenyl-1,2,3,6-tetrahydropyridin-1-yl)propoxy]phenyl}thiazolidine-3-carbothioamide hydrochloride.

10. The compound according to claim 1, which is N-methyl-2-{2-[3-(4-phenyl-1,2,3,6-tetrahydropyridin-1-yl)ethyloxy]phenyl}thiazolidine-3-carbothioamide hydrochloride.

11. A compound according to claim 1 in its racemic form.

12. A compound according to claim 1 in its optically active form.

13. A pharmaceutical composition exhibiting a cardiotonic effect which comprises a therapeutically effective amount of a compound of the formula:

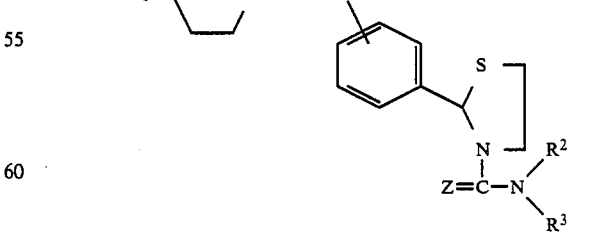 (I)

wherein R¹ is an unsubstituted phenyl group or a phenyl group substituted with a member selected from the group consisting of a halogen atom, a lower alkyl group, and a lower alkoxy group, R² is hydrogen or a lower alkyl group, R³ is hydrogen, a lower alkyl group or a lower alkanoyl group, Q is a single bond or a lower alkylene group, Alk is a lower alkylene group, Y and Z are the same or different and are an oxygen atom or a sulfur atom and the group of the formula:

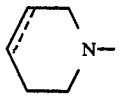

is either

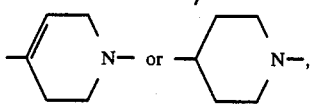

or a pharmaceutically acceptable salt thereof, and a pharmaceutically acceptable carrier.

14. The composition according to claim 13, wherein $R^1$ is unsubstituted phenyl or phenyl substituted with fluorine, methyl or methoxy, $R^2$ is hydrogen or methyl, $R^3$ is hydrogen, methyl, ethyl, butyl or acetyl, Q is a single bond or methylene, and Alk is ethylene or trimethylene.

15. The composition according to claim 14, wherein $R^1$ is phenyl, 3-fluorophenyl, 3-methylphenyl, 3-methoxyphenyl or 4-methoxyphenyl.

16. A pharmaceutical composition exhibiting a cardiotonic effect which comprises a therapeutically effective amount of a compound according to claim 4.

17. A method for producing a cardiotonic effect on a warm-blooded animal comprising administering to said warm-blooded animal an effective amount of a compound of the formula:

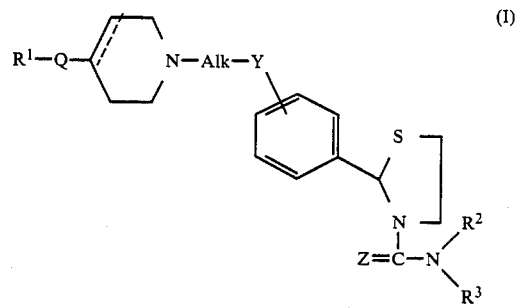 (I)

wherein $R^1$ is an unsubstituted phenyl group or a phenyl group substituted with a halogen atom, a lower alkyl group or a lower alkoxy group, $R^2$ is hydrogen or a lower alkyl group, $R^3$ is hydrogen, a lower alkyl group or a lower alkanoyl group, Q is a single bond or a lower alkylene group, Alk is a lower alkylene group, Y and Z are the same or different and are an oxygen atom or a sulfur atom and the group of the formula:

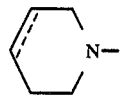

is either

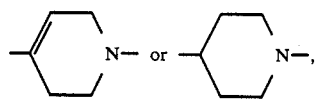

or a pharmaceutically acceptable salt thereof.

18. The method according to claim 17, wherein the effective amount is in a range of 0.01 to 100 mg/kg/day.

19. The method according to claim 17, wherein said effective amount of said compound is administered orally or parentally.

20. The method according to claim 17, wherein $R^1$ is an unsubstituted phenyl group or a phenyl group substituted with fluorine, methyl or methoxy, $R^2$ is hydrogen or methyl, $R^3$ is hydrogen, methyl, ethyl, butyl or acetyl, Q is a single bond or methylene, and Alk is ethylene or trimethylene.

21. The method according to claim 20, wherein $R^1$ is phenyl, 3-fluorophenyl, 3-methylphenyl, 3-methoxyphenyl or 4-methoxyphenyl.

* * * * *